United States Patent [19]

Taira et al.

[11] Patent Number: 5,500,357
[45] Date of Patent: Mar. 19, 1996

[54] RNA TRANSCRIPTION SYSTEM USING NOVEL RIBOZYME

[75] Inventors: Kazunari Taira; Satoshi Nishikawa, both of Tsukuba; Hidekatsu Maeda, Nagareyama, all of Japan

[73] Assignee: Agency of Industrial Science & Technology, Ministry of International Trade & Industry, Tokyo, Japan

[21] Appl. No.: 55,390

[22] Filed: May 3, 1993

Related U.S. Application Data

[63] Continuation-in-part of Ser. No. 677,427, Mar. 29, 1991, abandoned.

[30] Foreign Application Priority Data

Nov. 2, 1990 [JP] Japan ..................... 2-298383

[51] Int. Cl.$^6$ .............. C12N 9/22; C12N 15/74; C12N 15/82; C12N 15/85
[52] U.S. Cl. .............. 435/91.31; 435/6; 435/172.3; 435/240.1; 435/240.2; 435/252.3; 435/320.1; 536/23.1; 536/23.2; 536/24.5; 514/44
[58] Field of Search ............ 536/23.1, 23.2, 536/24.5; 514/44; 435/91.1, 6, 91.21, 91.3, 91.31, 91.4, 172.3, 320.1, 252.3, 240.1, 240.2

[56] References Cited

PUBLICATIONS

Taira et al. (1990), Protein Engineering, vol. 3, No. 8, pp. 733–737.
Hutchins et al. (1986), Nucleic Acid Res., vol. 14, pp. 3627–3640.
Gerlach et al., Virology, vol. 151, pp. 172–185.
Cotten et al. (1989), EMBO J., vol. 8, pp. 3861–3866.
Diener et al. (1989), Proc. Natl. Acad. Sci., vol. 86, pp. 9370–9374.
Dzianott et al. (1989), Proc. Natl. Acad. Sci., vol. 86, pp. 4823–4827.

*Primary Examiner*—Jacqueline M. Stone
*Assistant Examiner*—J. LeGuyader
*Attorney, Agent, or Firm*—Oblon, Spivak, McClelland, Maier & Neustadt

[57] ABSTRACT

The invention provides a recombinant plasmid containing a sequence encoding any genes inserted between 5' and 3' self-cleavage ribozymes. The recombinant plasmid can be amplified in vivo as well as in vitro while growing the host cell. When obtaining RNA transcripts of the inserted sequence, the recombinant plasmid does not require a restriction enzyme digestion step (run-off transcription) since cis-acting ribozymes perform self-catalyzed cleavage at 5' and 3' sides of the inserted sequence once it is transcribed. In this specific example, the trans-acting RNA enzyme sequence is inserted between 5' and 3' cleavage ribozymes. However, the trans-acting ribozyme sequence in the recombinant plasmid can be replaceable with any other sequence (e.g., antisense RNA, RNAs of HIV-1, HDV and other RNA viruses etc.). This construct is especially useful since each unit, consisting of 5' processing ribozyme, inserted sequence, and 3' processing ribozyme, can be connected in tandem. By so doing, ribozymes targeted to various sites can initially be transcribed as a long RNA chain which subsequently undergoes cleavage to produce independent trans-acting ribozymes, each possessing a specific target site.

6 Claims, 17 Drawing Sheets

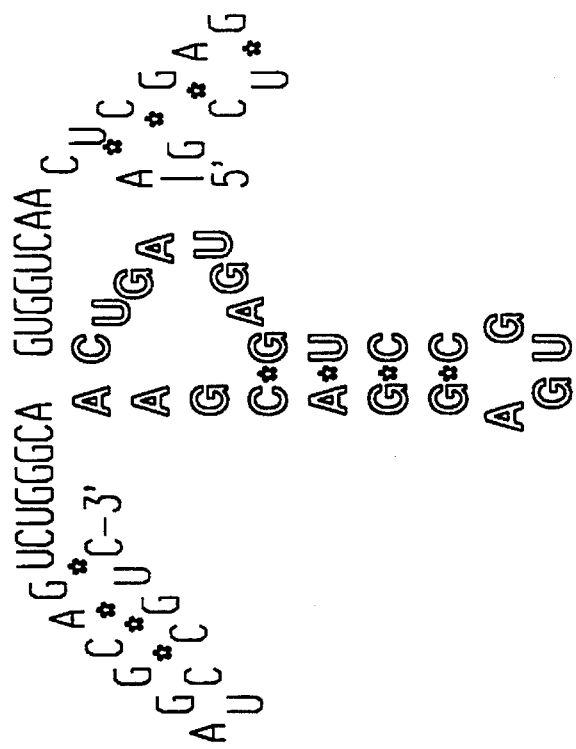
FIG. 4

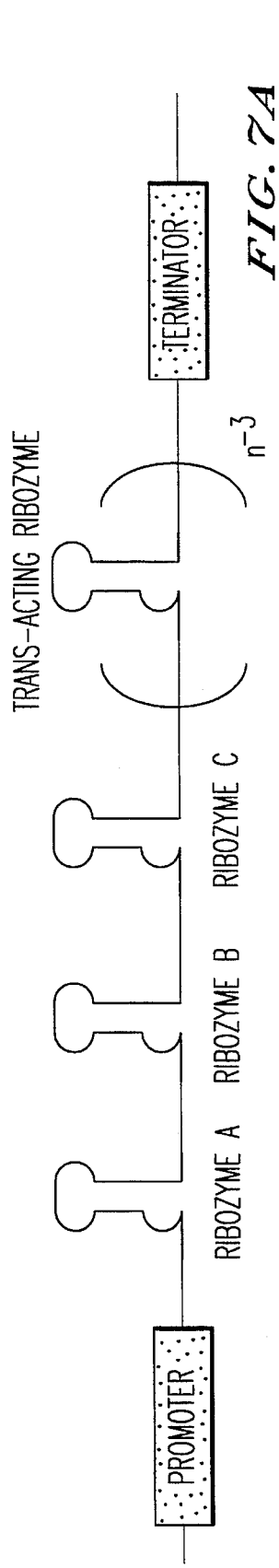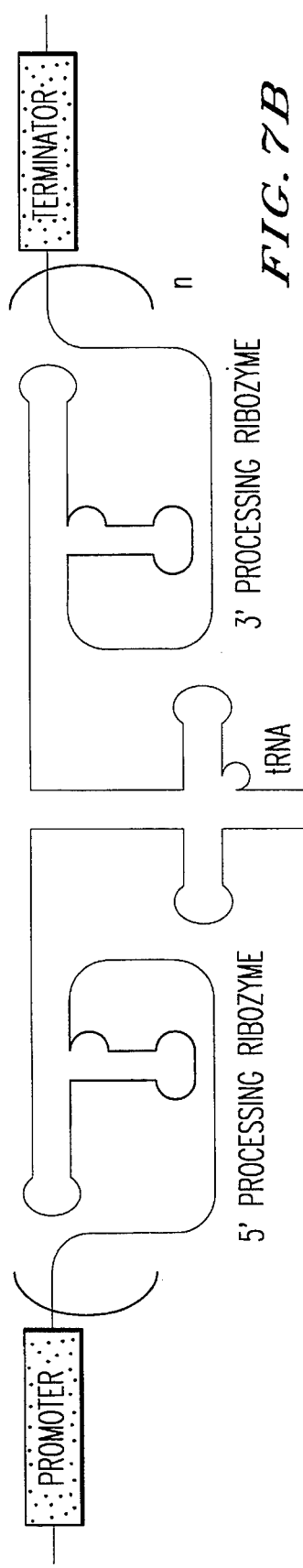

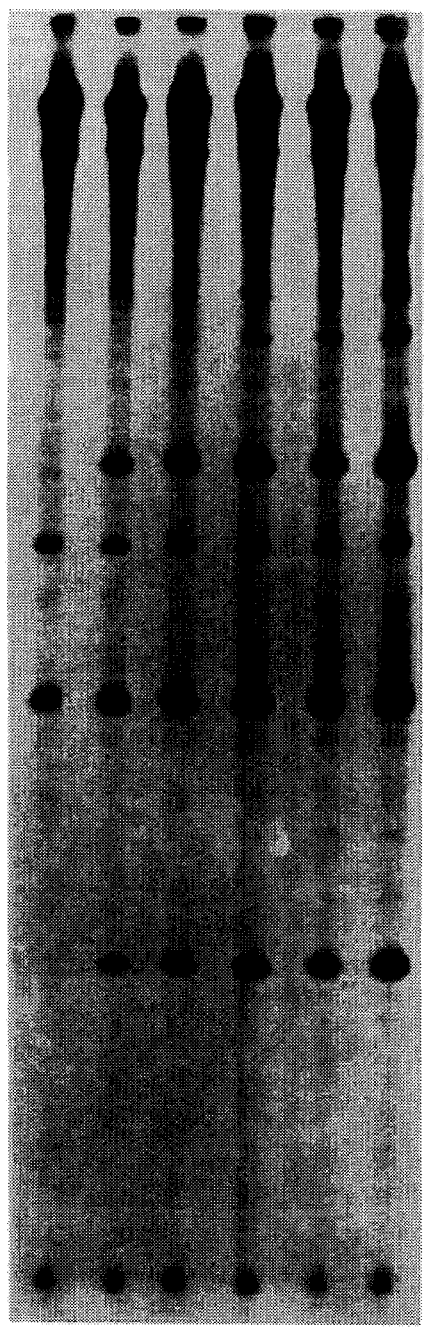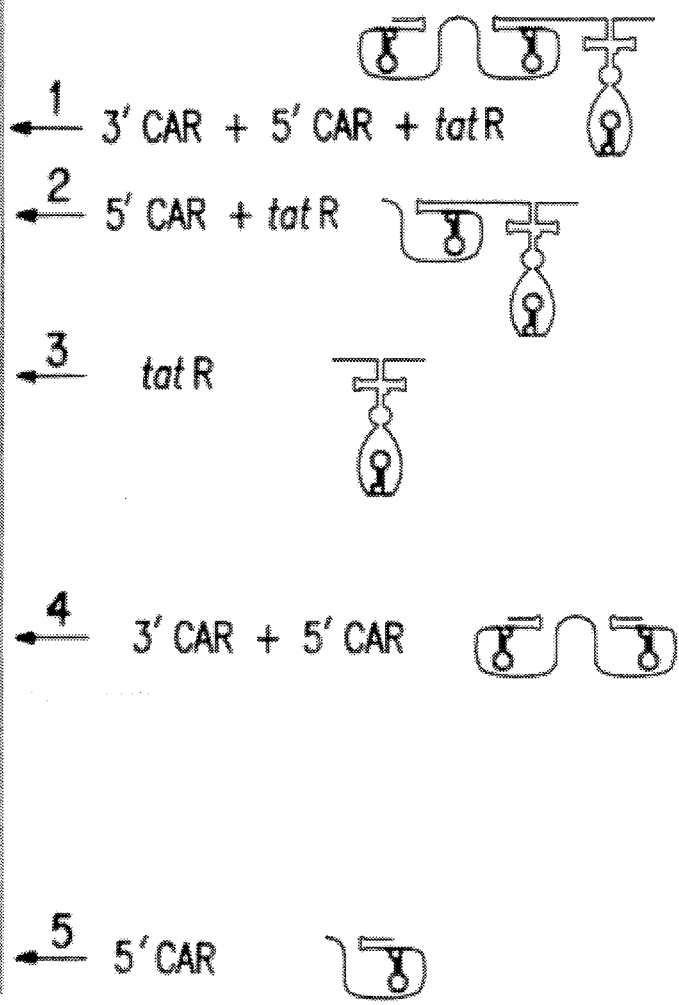
FIG.12(A)

1

RNA TRANSCRIPTION SYSTEM USING NOVEL RIBOZYME

CROSS-REFERENCE TO RELATED APPLICATION

This is a continuation-in-part application of patent application Ser. No. 07/677,427 filed on Mar. 29, 1991 now abandoned.

BACKGROUND OF THE INVENTION

It had been long believed that enzyme was protein until the discovery of ribozyme, an RNA segment with endoribonuclease activity, in 1981. The discovery has changed the conventional belief dramatically. Thomas Cech found that the precursor of a ribosomal RNA (rRNA), inTetrahymera (protozoan) undergoes self-splicing in the absence of proteins. The intron (IVS) in this precursor RNA molecule is precisely removed by a catalytic activity of the RNA itself (Nature, 308: 820–825, 1984). Subsequently, catalytically active RNA molecules that act for the cleavage of phosphodiester bond have been found one after another. Symons has found conserved ribozyme sequence in several plant viruses and Haseloff and Gerlach have constructed a synthetic ribozyme with a catalytic domain of 24 bases (Nature, 334: 585–591, 1988).

FIG. 1 shows the structure of a synthetic ribozyme comprising a binding segment C which recognizes the sequence of an RNA molecule (substrate) and forms a base-pairing with the substrate, and a catalytically active segment B containing a specific 24-nucleotide [SEQ ID No: 1]. The site A contains sequences in the substrate, immediately adjacent to the site of cleavage (indicated by arrow). The site A can be other bases, although FIG. 1 shows GUC.

Haseloff, J., et al., constructed synthetic ribozymes as follows: The ribozyme sequences were synthesized as single-stranded oligonucleotides. The oligonucleotides were ligated to plasmid DNA, and after transformation, DNA of the resulting clones were digested with restriction enzyme. The plasmids containing a sequence encoding synthetic ribozymes were recovered. The plasmids were used after linearization for transcription in vitro. Then, synthetic enzymes were obtained. They designed three types of oligomers encoding three different ribozymes and demonstrated that these ribozymes cleaved the CAT gene transcript at three different sites.

The conventional method, called a run-off method, requires an extra step (restriction enzyme digestion) as described below. The recombinant plasmid containing the DNA fragment encoding a gene of interest is first digested with restriction enzyme at the 3' end of the gene and then the fragment is used for in vitro transcription to give RNA enzyme. When the recombinant plasmid is transcribed without restriction enzyme digestion, an extra flanking sequence is also attached at 3' side of the transcribed gene product. The digestion step is therefore designed for removing the extra sequence at 3' side. In order to avoid the extra segment at 5' side the DNA fragment at 5' end is designed to be located immediately downstream of a promoter sequence. For the DNA fragment at 3' end, there has been no alternative method but a run-off method using restriction enzyme since no universal terminator has been found (FIG. 2). Haseloff, J., et al., also synthesized ribozymes using the run-off method.

Hereafter, the gene of interest to be transcribed is a trans-acting ribozyme. However, the discussion is general and applicable to any sequences <genes). Although a ribozyme has been obtained through restriction enzyme digestion and subsequent in vitro transcription using a linearized DNA as a template (run-off transcription), this method cannot be used in vivo since there is no restriction enzyme which specifically cuts at 3' end of the ribozyme-coding DNA template. In addition, an extra nucleotide sequence is found bound to the sequence of the ribozyme after transcription unless the 5' end of the DNA fragment encoding ribozyme is placed immediately downstream of a promotor. The conventional method therefore has three major points to improve. Firstly, a digestion step in the procedure can be eliminated. Secondly, the ribozyme can be amplified in vivo while the host cell harboring the recombinant DNA encoding the ribozyme is kept growing. Thirdly, the extra nucleotide sequence can be removed from the ribozyme.

An object of the invention provides a recombinant DNA containing novel synthetic ribozyme sequences which can be utilized as a template being an intact closed circular form without restriction enzyme digestion. The recombinant DNA can be produced in vivo while the host cell is kept growing and produces a ribozyme free of an extra nucleotide sequence.

Moreover, when ribozymes are to be used as anti-HIV agents (Sarver, M., Cantin E., Chang, P., Ladne, P., Stephens, D., Zaia, J. & Rossi, J. (1990) Science 247, 1222–1225), one has to consider genetic variability of HIV. HIV is infamous for its high mutation rate caused by the low fidelity of its reverse transcriptase which lacks the function of proof-reading and has a tendency to add an extra nucleotide upon DNA template jumps. This mutability of HIV not only makes it difficult to prepare vaccines against HIV but also hinders the application of ribozymes toward HIV RNA cleavage because of the high substrate-specificity of the ribozyme. One way to overcome this mutability of HIV in applying ribozymes is to target several conserved sites simultaneously. Then, even if one or more sites undergo mutations to avoid cleavages by ribozymes, the other conserved sites can potentially be cleaved by other ribozymes which have been targeted to those sites.

There seems to be at least two ways to express multitargeted-ribozymes: the simpler way is just to join several sequences of ribozymes possessing different target sites in tandem so that all the transcribed multitargeted-ribozymes would be connected in tandem into a single RNA (connected-type); the other strategy is to combine cis-acting ribozymes with trans-acting ribozymes so that the several trans-acting ribozymes targeted to HIV (or any other sequences) would be trimmed at both 5' and 3'-ends by the actions of cis-acting ribozymes, liberating several trans-acting ribozymes which would work independently of others (shotgun-type). However, kinetic behaviors of the above mentioned two types of expression systems for multitargeted-ribozymes are unknown and need to be examined.

SUMMARY OF THE INVENTION

Present inventors have found that the above object is achieved by constructing a recombinant DNA in which a DNA encoding a trans-acting ribozyme of interest is ligated to DNAs encoding another cis-acting ribozymes which serve to cleave the 5' and 3' ends of the trans-acting ribozyme of interest. Moreover, by connecting the whole units in tandem (shotgun-type expression system), several trans-acting ribozymes, trimmed at both 5' and 3' ends, are generated, that activities are proportional to the number of the units connected in tandem, whereas the activities of simply connected ribozymes reach plateau values after connection of 3 units. Therefore, the shotgun-type ribozymes have been proven to be kinetically superior to the connected-type ribozymes.

The invention comprises;

(1) A recombinant plasmid containing a sequence encoding a trans-acting hammerhead-type ribozyme flanked by 5' and 3' self-cleavage cis-acting hammerhead-type ribozymes, which produces a long RNA transcript that undergoes self-catalyzed cleavage at the 5' and 3' sides of the inserted RNA.

(2) A recombinant plasmid containing 1-100 units of a trans-acting hammerhead-type ribozyme flanked by 5' and 3' self-cleavage hammerhead-type ribozymes, which produces an equivalent number of the RNA transcript connected in tandem that undergoes self-catalyzed cleavage at the 5' and 3' sides of the trans-acting ribozyme.

1-100 molecules of trans-acting ribozymes each embedded into tRNA are produced per one RNA transcript.

(3) A method of producing the RNA transcripts self-cleaved at 5' and 3' sides which are transcribed from the recombinant plasmid of (1) or (2) that act as templates.

(4) A trasformant comprising a cell of bacteria which is transformed with the recombinant plasmid of (1) or (2).

DESCRIPTION OF THE FIGURES

FIG. 4 shows the structure and nucleotide sequence [SEQ ID No. 4] of a SFL1 ribozyme and schematic model for the binding of the SFL1 ribozyme to a SFL1 mRNA.

FIG. 7(a) shows the design of multiple ribozymes supposedly targeting corresponding RNAs. The ribozymes of the design do not cleave RNA targets as effectively as the one shown in FIG. 7(b): Individual ribozymes in a single long RNA transcript are hardly directed toward various RNA targets. Also, the homologous sequence of ribozyme within the long RNA transcript may lump together and ribozymes are unable to function as expected.

FIG. 7(b) shows our proposed design for multiple ribozymes. The number of ribozymes may be n wherein n is between 1 and 100. A unit of the ribozyme comprises a 5' block, a trans-acting ribozyme/tRNA and a 3' block. The trans-acting ribozyme/tRNA can be designed to target a specific RNA. The 5' and 3' sides of the trans-acting ribozyme/tRNA are cleaved by 5' and 3' self-cleavage ribozymes and each trans-acting ribozyme/tRNA is free to be directed toward a specific RNA target.

FIG. 8 shows more general description of pGENE8459 series vector[SEQ ID NOS:2, 5–6]. Any sequence can be inserted into the DNA template region.

FIG. 12 shows effects of the number of units connected in tandem for the shotgun-type vector shown in FIG. 11B. (A): Transcription and trimming reactions were followed by electrophoresis, 6 h after initiation of the transcription. Note that the amount of trans-acting ribozymes (band 3) increases with the number of units connected in tandem, although, in all cases, identical amount of DNA templates were used. The identical amount of DNA templates can be confirmed by bands 2 and 5, that show the same amount of transcripts in all cases. (B): Relative rates of transcriptions from various templates coding the shotgun-type ribozymes (n=1~10). The amount of trans-acting ribozymes transcribed from the template with n=1 at 6 h was taken as unity and the transripts derived from the other templates were calculated relative to that.

DETAILED DESCRIPTION OF THE INVENTION

In order to construct a recombinant plasmid containing the sequence encoding a trans-acting ribozyme having 5' and 3' self-cleavaging cis-acting ribozymes, we have combined three blocks, a 5' block comprising the sequence encoding a 5' cis-acting ribozyme and the 5' binding sequence containing its self-cleavage site, a trans-acting ribozyme block comprising the sequence encoding a trans-acting ribozyme of interest and the target binding sequence, and a 3' block comprising the sequence encoding a 3' ribozyme and the 3' binding sequence containing its self-cleavage site. The 5' block self-cleaves the 5' side of the trans-acting ribozyme block. The DNA sequence of the 5' block is ligated upstream of the trans-acting ribozyme block. The 3' block self-cleaves the 3' side of the trans-acting ribozyme block. The 3' block is located downstream of the trans-acting ribozyme block.

The recombinant plasmid of the invention produces RNA transcripts in vivo (yeast, fungi, plant cell, animal cell) as well as in vitro. Transcription starts at transcription initiation site (+1) downstream of a promoter, moves down in the 3' direction without stop even at the 3' end of the 3' block, resulting in a longer RNA transcript than the concatameric unit. The long RNA transcript undergoes self-catalyzed cleavage at the 5' and 3' sides of the trans-acting ribozyme block and the resulting trans-acting ribozyme does not have extra sequences at both sides.

Figure 3:
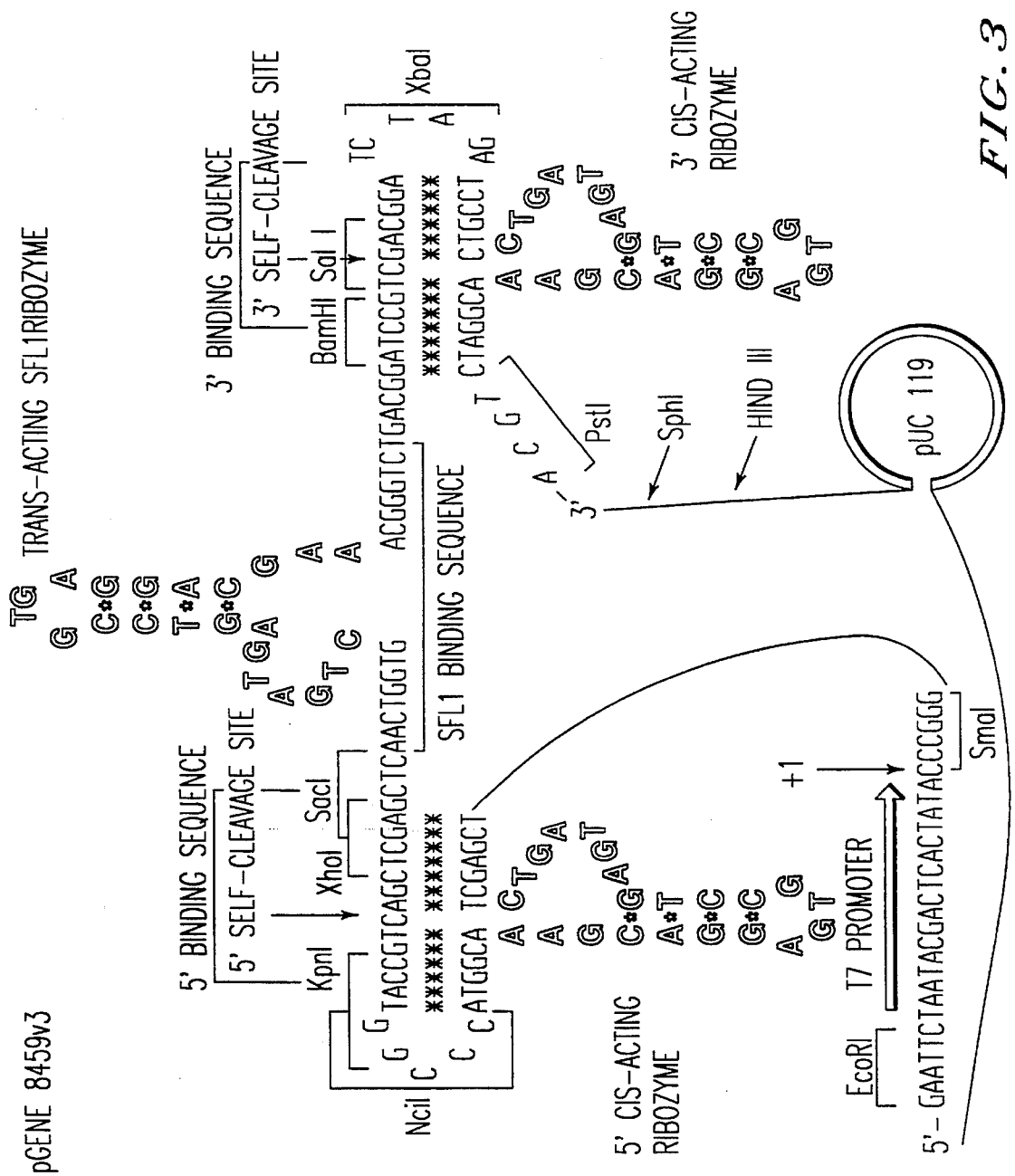

FIG. 3 shows a specific recombinant plasmid (pGENE8459v3) containing the sequence [SEQ ID NOS:2–3] encoding a new trans-acting SFL1 ribozyme having 5' and 3' self-cleavage cis-acting rebozymes; the trans-acting SFL1 ribozyme cleaves SFL1 mRNA of yeast (SFL1 gene relates to a flocculent property of yeast). The EcoRI/SacI site of pGENE8459 (previously described by Taira, K., et al., Japanese Patent Appln. No. 329831/1989 and Taira, K., et al., Protein Engineering 3: 733–737 (1990) is replaced by a chemically synthesized oligonucleotide: The EcoRI/SacI sequence shown in FIG. 3 and the sequences are chemically synthesized and the 5' end of oligonucleotides are phosphorylated. The annealed EcoRI/SacI fragment is inserted into the EcoRI/SacI site of pGENE8459.

The structure of the novel trans-acting ribozyme having 5' and 3' self-cleavage ribozyme comprises a promoter for T7 RNA polymerase, a SFL1 binding site which recognizes a SFL1 mRNA sequence, a stem and loop-like structure of SFL1 ribozyme which cleaves SFL1 mRNA, a 5' binding sequence containing its self-cleavage site which is recognized and cleaved by a 5' ribozyme, a stem and loop-like structure of the 5' ribozyme which cleaves at its 5' self-cleavage site, a 3' binding sequence containing its self-cleavage site which is recognized and cleaved by a 3' ribozyme and a stem and loop-like structure of the 3' ribozyme which cleaves at its 3' self-cleavage site.

In the 5' binding sequence containing its self-cleavage site and the 3' binding sequence containing its self-cleavage site, the double-strands are complementary and form base-pairing except for a base immediately upstream of their self-cleavage site. Transcription starts at +1 site downstream of T7 promoter and moves in the 3' (downstream) direction. The RNA transcript undergoes self-catalyzed cleavage at the 5'-and 3'-self-cleavage sites by the action of 5'- and 3-ribozymes, respectively. The final RNA transcript, which is a trans-acting ribozyme, does not contain extra sequences at both 5' and 3' sides.

The resulting trans-acting ribozyme and its nucleotide sequence [SEQ ID NO: 4] are shown in FIG. 4. The trans-acting ribozyme contains a base-pairing structure at the 5'- and 3'-end segments and forms a hair-pin structure which makes the trans-acting ribozyme stable to exonclease activity in vivo. The trans-acting ribozyme can be better stabilized by embedding it inside a tRNA sequence as later shown in FIG. 7(b). The materials including the SFL1 ribozyme for cleaving SFL1 mRNA, the T7 promoter for T7 RNA polymerase and pUCl19 which are utilized to construct the recombinant plasmid, do not limit the scope of the invention.

Although the recombinant plasmid in FIG. 3 is designed to produce the trans-acting ribozyme, the recombinant plasmid can be used to produce various RNA transcripts such as RNAs of RNA viruses and anti-sense RNAs simply by replacing the trans-acting ribozyme block (See FIG. 3) with a sequence of interest. SP6, GAL7, SV40, SRα and various other promoters can be utilized as a promoter of the recombinant plasmid. A suitable vector can be the one capable of producing an RNA transcript in various organisms and selected according to the organisms (e.g., plant, animal).

In addition, a recombinant plasmid can be designed to contain a number of various concatameric units as shown in FIG. 7(b). The whole concatameric unit (1–100 units) is placed between a promoter and a terminator or within any genes undergoing transcription. A unit of the concatamer comprises a 5' block, a trans-acting ribozyme embedded into tRNA in order to stabilize the trans-acting ribozyme (hereafter referred to as trans-acting ribozyme/tRNA) and 3' block. The 5' and 3' blocks serve to cleave the 5' and 3' sides of the trans-acting ribozyme/tRNA. The tRNA serves to stabilize the trans-acting ribozyme which cleaves an RNA target. The trans-acting ribozyme can be specially designed to target a specific RNA; each concatameric unit can be designed to target at different RNAs. The recombinant plasmid containing various concatameric units targeted at different sites of the target RNA gene is therefore especially useful to target RNAs arisen from microorganisms of a high mutation rate. The env gene of human immunodeficiency virus type 1 (HIV-1) and others are, for example, known to undergo mutation at a very rapid rate. The recombinant plasmid may be used to cleave the RNAs of these viruses by simultaneously targeting various sites. The recombinant plasmid containing various concatameric units also have the advantages as described above (e.g., the host cell containing the recombinant plasmid is grown while producing a number of various concatameric units).

Figure 11A:
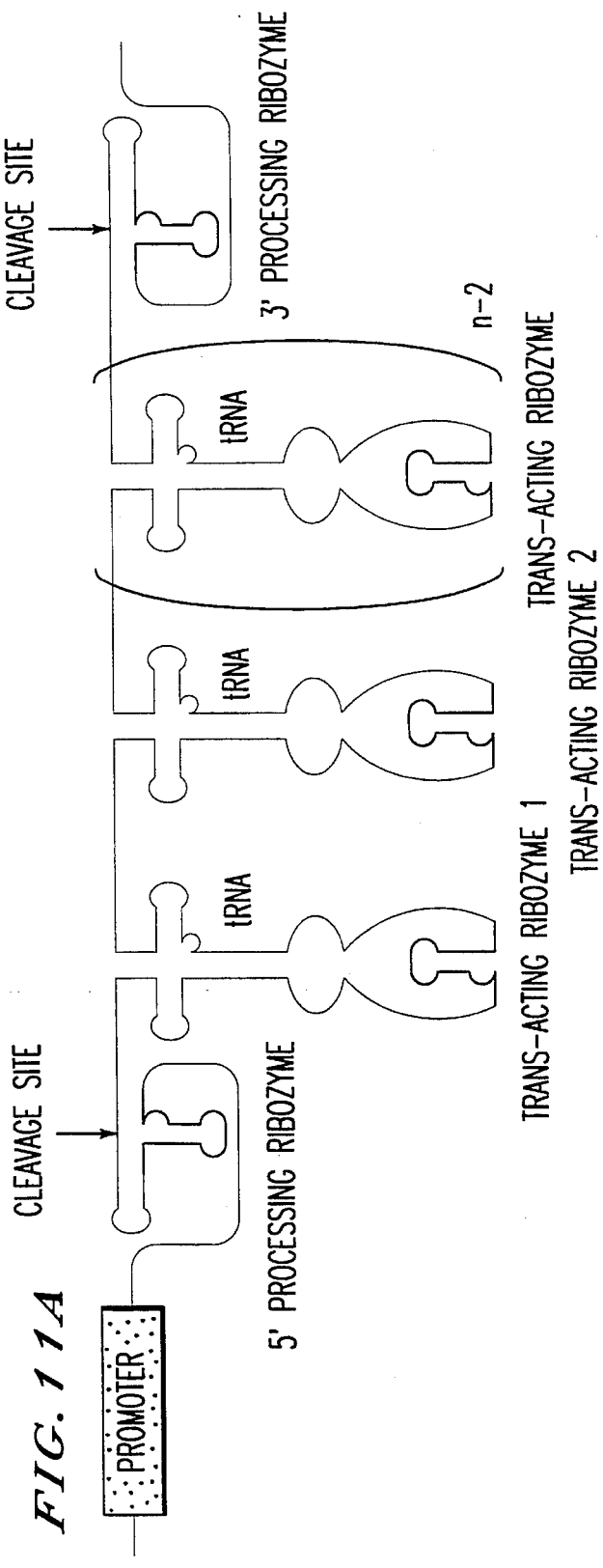
FIG. 11 shows two kinds of multiple ribozyme expression systems, corresponding to FIG. 7, which are used to compare the mutual reactivity difference. (A):Simply connected-type ribozyme expression vector. Several tRNA-embedded trans-acting ribozymes are simply connected in tandem. Therefore, trans-acting ribozymes are transcribed as a single RNA molecule. To facilitate the analysis of transcription products, cis-acting ribozyme sequences are added at each 5' and 3'-extreme-ends. (B): Shotgun-type ribozyme expression vector. Several units of whole 5' and multitargeted-ribozymes 3'-trimming vector, similar to that shown in FIG. 9, are connected in tandem. Upon transcription, several independent trans-acting ribozymes are liberated.
Figure 11B:
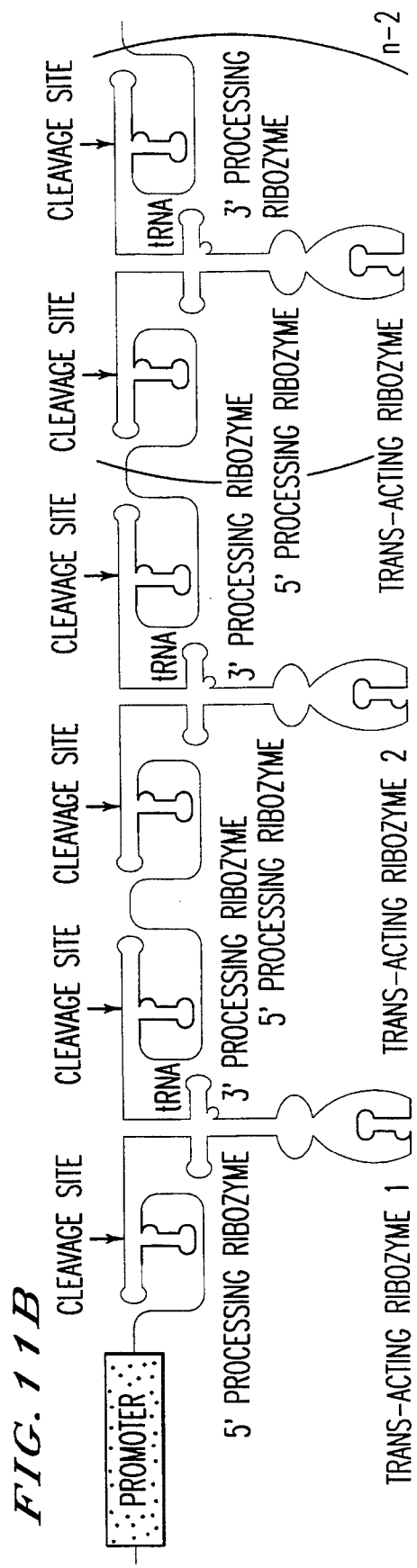

Moreover, this kind of unit, consisting of trans-acting ribozyme flanked by 5' and 3' cis-acting ribozimes, can be multiply connected in tandem. Kinetic behaviors of ribozymes derived from two types of multiple-ribozimes expression vectors are examied. In one case, multiple-ribozymes are expressed as a single RNA molecule where all the ribozymes are simply connected in tandem (connected-type; FIG. 3A). In the other case, multiple-ribozymes are flanked by cis-acting ribozymes at both 5' and 3'-ends so that, upon transcription, multiple-ribozymes are trimmed at both 5' and 3'-ends, resulting in liberation of multiple independent ribozymes (shotgun-type; FIG. 11B). When levels of ribozyme expressions are examined, for the shotgun-type vector, the amount of ribozyme transcript is proportional to the number of units (n) connected in tandem. Accordingly, the activities of the shotgun-type ribozymes, for the cleavage of HIV-1 RNA in vitro, are also proportional to the number of units connected in tandem (n). On the other hand, the activities of the connected-type ribozymes reach plateau values at around n–3. These results indicate that, employing the shotgun-type expression system, it is possible to generate various independent ribozymes, each possessing different target site, without sacrificing activities of each ribozymes. The usefulness of shotgun-type expression system is not limited to only ribozymes; any independent antisense RNA can similarly be produced. Having combined several multiple target sites, it is possible that one shotgun-type expression system provides an immune system against both HIV-1 and HIV-2, or several sub-groups of HIV-1. Even for a specific HIV-1 treatment, targeting several or all conserved sites should fight favorably against the genetic variability of HIV.

Figure 1:
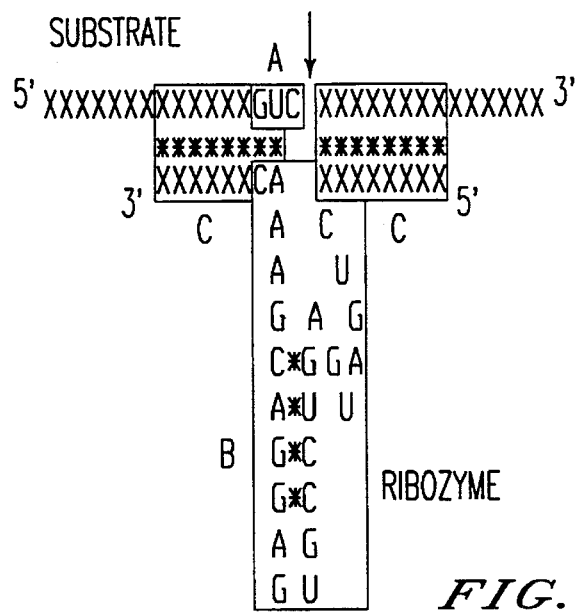
FIG. 1 shows a Haseloff & Gerlach model for the design of ribozymes.
Figure 2A:
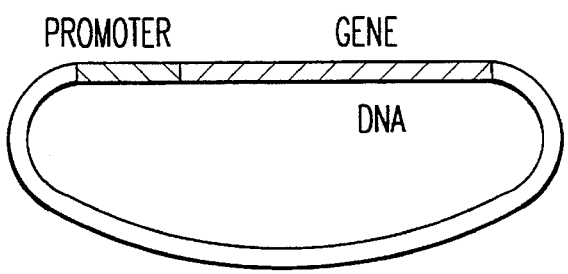
FIG. 2 shows a conventional run-off method schematically.
Figure 2B:
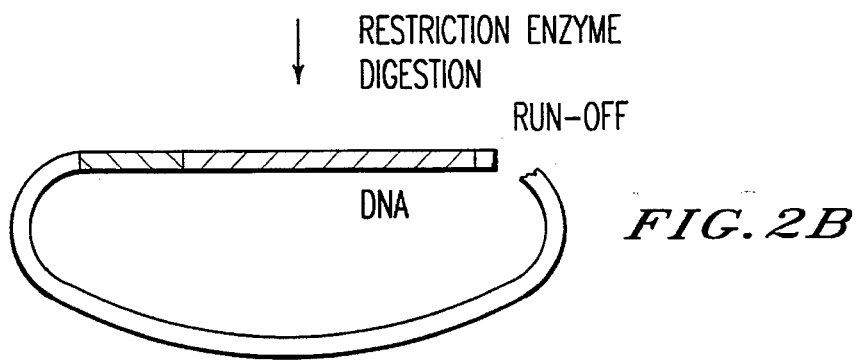
Figure 2C:
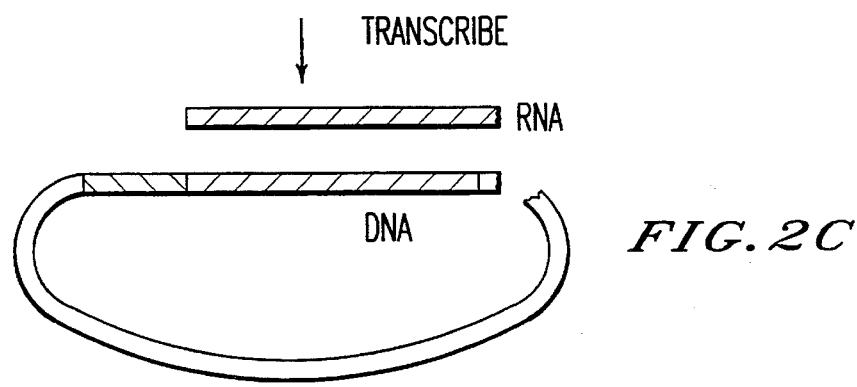
Figure 5:
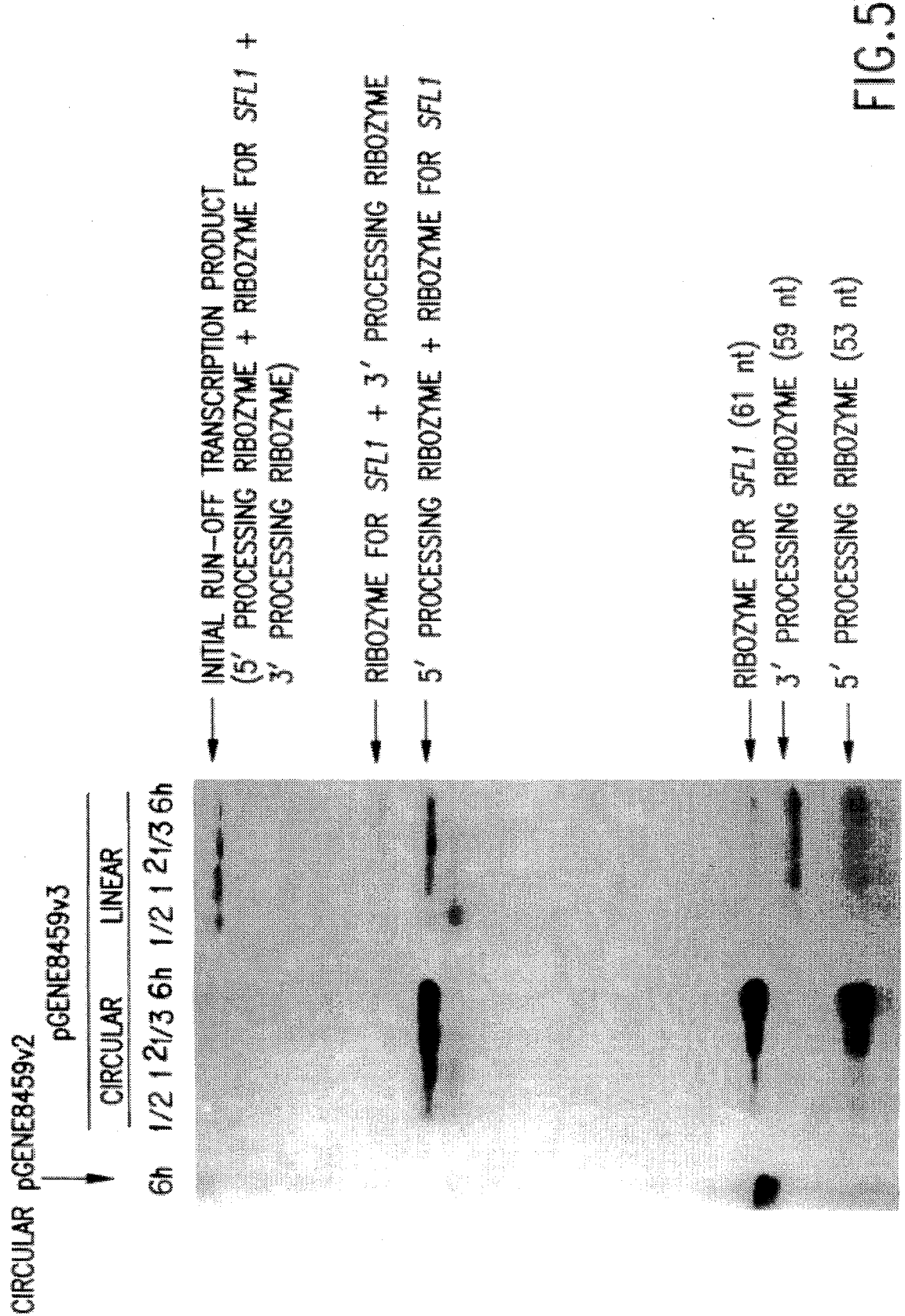
FIG. 5 shows the autoradiogram of ccc pGENE8459v3 (lanes A–D) transcripts and HindIII-linearized pGENE8459v3 (lanes E–H) transcripts.

A recombinant plasmid containing the sequence encoding a trans-acting ribozyme having 5' and 3' self-cleavage ribozymes can produce a novel trans-acting ribozyme free of unwanted sequence at its 5' and 3' flanking region without digesting the plasmid with restriction enzyme: The recombinant plasmid does not require the time-consuming digestion step as in run-off transcription. In addition, the recombinant plasmid can produce the novel trans-acting ribozyme in vivo as well as in vitro: The recombinant plasmid can be amplified in vivo while producing the novel trans-acting ribozyme. Furthermore, transcription efficiency of a covalently closed circular (ccc) pGENE8459v3 is far better than that of a linearized DNA (i.e., run-off method, see FIG. 2) as illustrated in FIG. 5. This is because, in case of the multitargeted-ribozymescovalently closed circular form, transcription occurs by a rolling circle mechanism. When isolating RNA, pGENE8459v3 method a higher level of purity than DNA used in the run-off method because both 5' and 3' ends are site-specifically cleaved in case of pGENE8459v3 transcripts.

EXAMPLE

The following Example further illustrates the invention.
(1) Construction of A Recombinant Plasmid pGENE8459v3

The EcoRI/ScaI sequence (see FIG. 3) [SEQ ID NOS:2–3] was chemically synthesized according to the method (Taira, K., Shinshi, H., Maeda, H., and Furukawa, K., 1990 Protein Engineering, 3: 733–737) and inserted into the EcoRI/SacI site of pGENE8459. A positive clone was obtained by screening of transformants using XhoI and the sequence was confirmed by a DNA sequencer (370A, Applied Biosystem).
(2) Transcription of the Recombinant Plasmid pGENE8459v3

Figure 6:
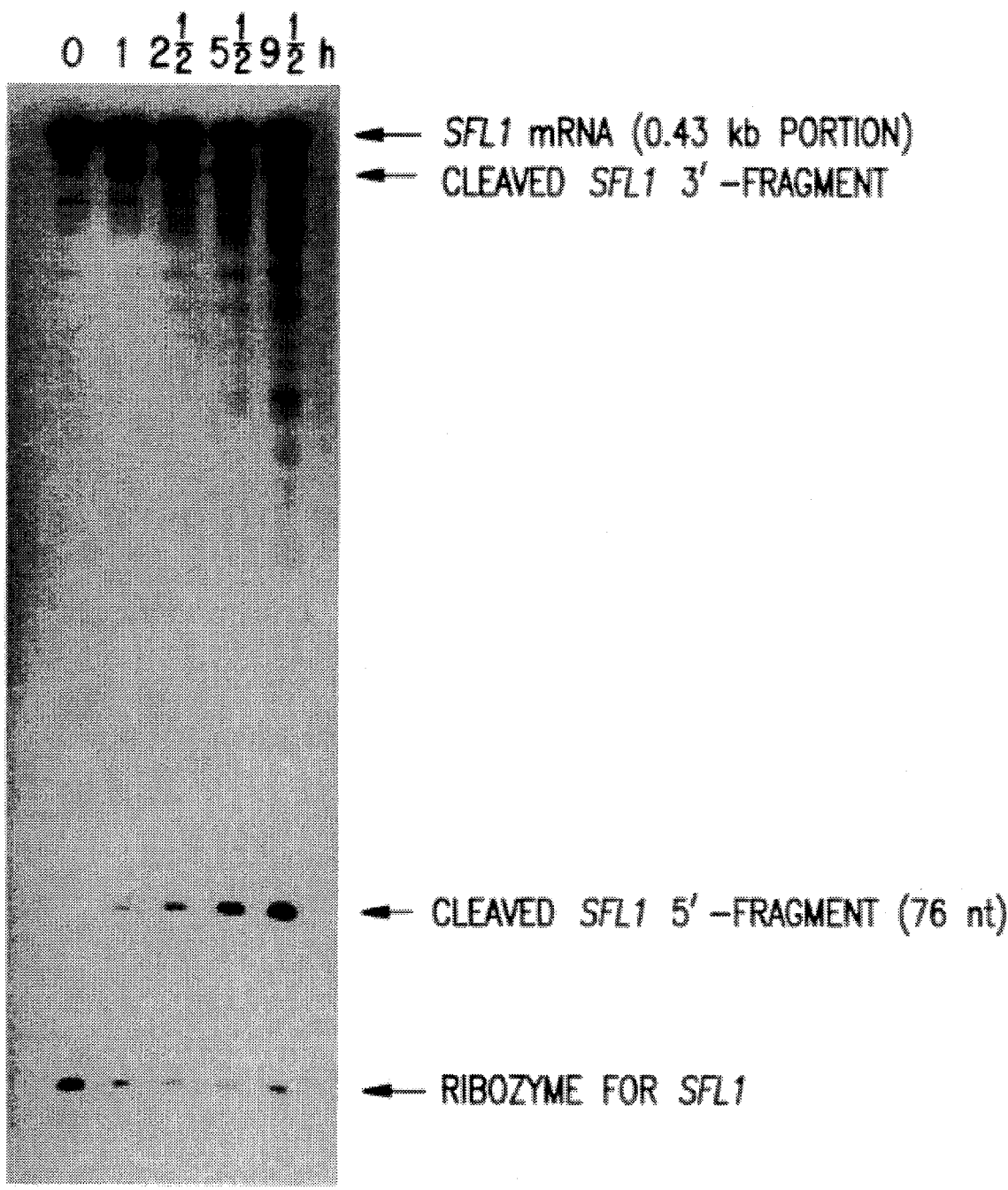
FIG. 6 shows cleavage of the SFL1 mRNA by the SFL1 ribozyme.

A novel trans-acting ribozyme was transcribed according to the method (Taira, K., et al., Japanese Patent Appln. No. 329831/1989 and Taira, K., Oda, M., Shinshi, H., Maeda, H.,
and Furukawa, K., 1990 Protein Engineering, 3: 733–737). The $^{32}$P-labelled labelled RNA transcript was electrophoresed on a 6% acrylamide gel containing 8.3% urea and autoradiographed as shown in FIG. 5. The sizes of the bands shown are in the range from about 50 to 130 bases. The ccc pGENE8459v3 was used for RNA transcription [lanes (A)–(D)] and the linearized pGENE8459v3 was used for RNA transcription [lanes (E)–(H)]. The time for transcription is 30 minutes in lanes (A) and (E), one hour in lanes (B) and (F), 2.5 hours in lanes (C) and (G), and 6 hours in lanes (D) and (H). The SFL ribozyme band (FIG. 5) was cut out of the gel and the band was placed in a tube.
(3) The reaction of ribozyme Similarly, PstI digested pAM19SFLlac (linear form) was transcribed and the RNA transcript (SFL1 mRNA) was electrophoresed on an acrylamide gel. The SFL1 mRNA band was cut out of the gel and the band was placed in a tube. 400 μl of buffer (0.3M sodium acetate, 0.1 mM EDTA, 20 mM Tris-HCl/pH 8.0) was added to each tube to extract RNA. After extraction, RNA was precipitated with ethanol. After RNA was recovered excess concentration of SFL1 mRNA (substrate) was combined with SFL1 ribozyme in buffer (50 mM Tris-HCl/pH 8.0, 10 mM $MgCl_2$). The mixture was incubated at 37° C. and the reaction was monitored at time=0 (lane A), 1 hour (lane B), 2.5 hour (lane C), 5.5 hour (lane D), and 9.5 hour (lane E ). The SFL1 mRNA formed a complex with the SFL1 ribozyme (as shown in FIG. 4 ) [SEQ ID NO: 4] and the SFL1 mRNA was cleaved into two segments.
A. FIG. 5 (A–D) shows the followings:

A ccc pGENE8459v3 transcript produced the 61-base band of SFL1 ribozyme, suggesting that the 5' and 3' ribozymes effectively cleaved during transcription at the 5' and 3' cleavage sites, respectively.
B. FIG. 5 (E–H) shows the followings:

When a linearized pGENE8459v3 (HindIII digestion, see the position in FIG. 3) was transcribed, a 5' ribozyme/SFL1 ribozyme /3' ribozyme concatamer was first produced and then gradually separated with time. Transcription efficiency of the liner form was low and extra by-product appeared.
C. FIG. 4 and 6 show the following:

The SFL1 binding sequence was designed to bind the SFL1 mRNA to cleave off at its +76 nucleotide when the SFL1 ribozyme acted on the SFL1 mRNA precisely (FIG. 4) [SEG ID NO: 4]. An SFL1 gene was transcribed using T7 RNA polymerase. The transcript was mixed with SFL1 ribozyme and 76 base transcript was found as expected (FIG.6).

Figure 8:
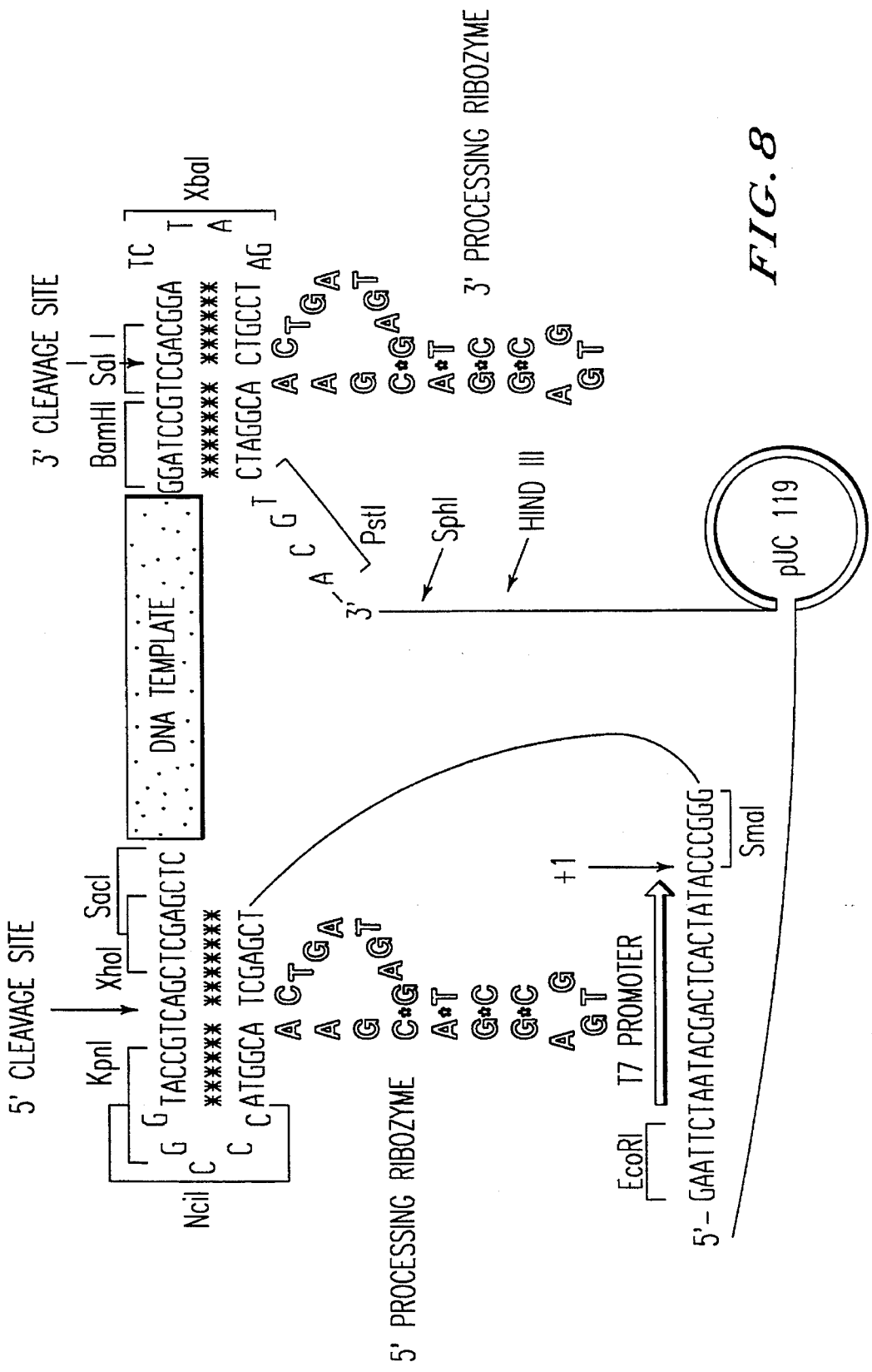
FIG. 8 shows the structure and nucleotide sequence [SEQ ID NOS: 2–8] of the trans-acting SFL1 ribozyme having 5' and 3' self-cleavage (cis-acting) ribozymes in the vector pUC119.
Figure 9A:
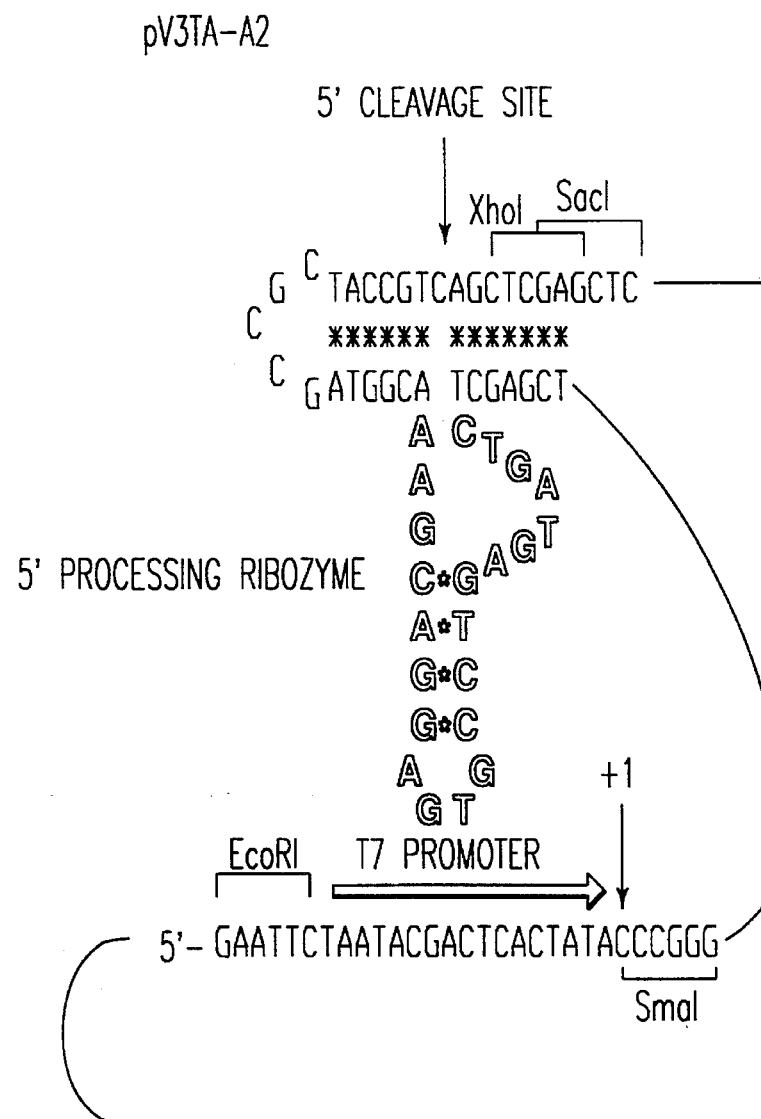
FIG. 9 shows a modified version of pGENE8459v3 shown in FIG. 3 (SEQ ID NOS:7–11). In this case trans-acting ribozyme is embedded into tRNA for stabilization in vivo as described by Cotten and Birnstiel (Cotten, M. & Birnstiel, M. (1989) EMBO J., 8, 3861–3866)(Yuyama, N., Ohkawa, J., Inokuchi, Y., Shirai, M., Sato, A., Nishikawa, S. & Taira, K. (1992) Biochem. Biophys. Res. Commun., 186, 1271–1279). Into the ApaI/EcoRV region, trans-acting ribozyme targeted to HIV RNA is inserted. And then several units, each consisting of trans-acting ribozyme flanked by 5' and 3' cis-acting ribozymes, are multiply connected in tandem to generate shotgun-type expression system of FIG. 11B.
Figure 9B:
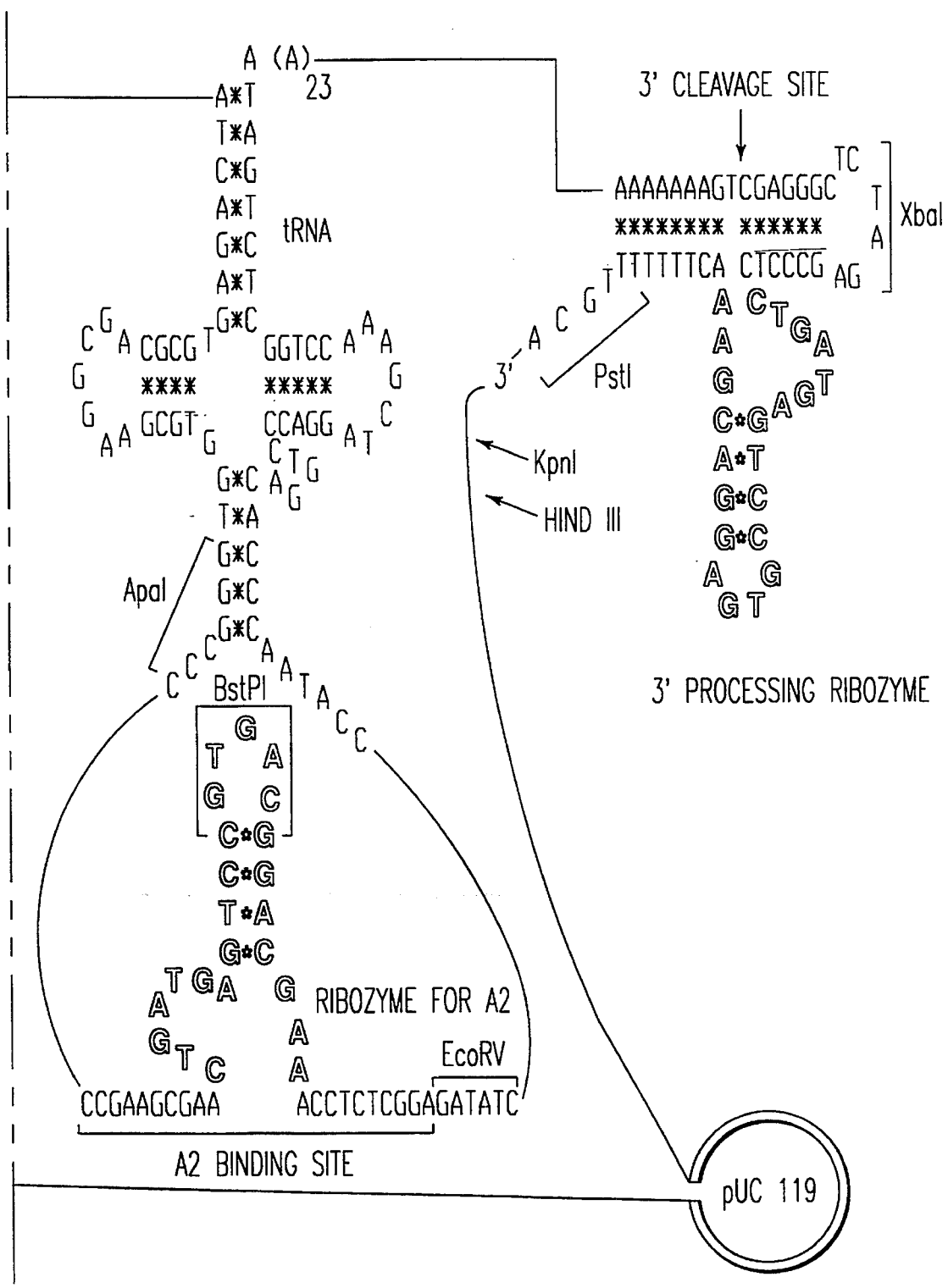

The recombinant plasmid of the invention does not require the digestion step of the template DNA. The 5' and 3' cis-acting ribozymes cleave their self-cleavage sites and the SFL1 trans-acting ribozyme cleaves the target SFL1 mRNA as predicted. The ccc pGENE8459v3 have advantages in transcription efficiency and purity as compared with a liner form (run-off transcription). The SFL1 binding sequence/SFL1 ribozyme block of pGENE8459v3 can be replaced by any other sequence as depicted in FIG. 8: pGENE8459v3 can be utilized to produce any RNA transcript and is especially useful for producing a short length RNA transcript in high purity. Moreover, the whole unit can be concatenated so as to increase the apparent copy numbers of the inserted sequence and/or to harbor multi-target sites in case of trans-acting ribozymes as illustrated in FIG. 7(b).
D. Construction of Multiple-Ribozyme Expression Plasmids Construction of the shotgun-type expression vectors are based on the modified pGENE8459v3 plasmid (FIG. 3), pV3T-A2 (Yuyama, N., Ohkawa, J., Inokuchi, Y., Shirai, M., Sato, A., Nishikawa, S. & Taira, K. (1992) Biochem. Biophys. Res. Commun., 186 1271–1279), in which Cotten and Birnstiel's tRNA-embedded ribozyme (Cotten, M. & Birnstiel, M. (1989) EMBO J., 8, 3861–3866) was combined with our trimming vector (Taira, K., Uebayashi, M., Maeda, H. and Furukawa, K. (1990) Protein Engineering, 3, 691–701; Taira, K., Nakagawa, K., Nishikawa, S & Furukawa, K. (1991) Nucleic Acids Res., 19, 5125–5130). The tRNA-embedded ribozyme portion of pV3TA-A2 (FIG. 9; [SEQ ID NOS:7–11]; ApaI/EcoRV fragment) was replaced by various ribozyme sequences possessing 8 bases as both substrate binding arms targeted to the relatively conserved HIV-1 RNA sequences (FIG. 10A) (SEQ ID NOS:12–16), that generates plasmids, each called pV3TA-HIV. During this process, PstI site was inserted into the stem II loop, replacing the BstPI site of pV3TA-A2, and the newly created unique PstI site was used for the identification of the successfully constructed ribozyme plasmids for HIV-1. We found out that the stem II and its loop region is inert in terms of catalysis and therefore can be used in gene manipulation (Yuyama, N., Ohkawa, J., Inokuchi, Y., Shirai, M., Sato, A., Nishikawa, S. & Taira, K. (1992) Biochem. Biophys. Res. Commun., 186, 1271–1279; Shimayama, T., Sawata, S., Komiyama, M., Komiyama, M., Takagi Y., Tanaka, Y., Wada, A., Sugimoto, N., Rossi, J.J., Nishikawa, F., Nishikawa, S. & Taira, K. (1992) Nucleic Acids Res. Symp. Ser., 27, 17–18).

In order to compare the in vitro ribozyme activities of simply connected multiple-ribozymes (connected-type; FIG. 11A) and that of independent multiple-ribozymes (shotgun-type; FIG. 11B), either the tRNA-embedded trans-acting ribozymes alone (FIG. 11A) or the whole unit of pV3TA-HIV, consisting of 5' and 3' processing ribozymes and the tRNA-embedded trans-acting ribozyme (FIG. 11B), were connected in tandem, in both cases, the number of repeat(s) ranging from 1 to 10 (FIG. 11). For this purpose, we have at first chosen a ribozyme sequence for tat-1 site (FIG. 11A) and connected this sequence in various units in the form shown in FIG. 11 (n=1–10).

E. Levels of Ribozyme Expressions from the Shotgun-Type Constructs

Levels of RNA expressions were examined using six shotgun-type constructs, each differing the number of ribozyme units connected in tandem (n=1–5, and 10 in FIG. 11B). Under the conditions we employed, the rate of transcription was linear up to 6 h. Shown in FIG. 12A are the transcription products examined after the transcription time of 6 h. The number of the units connected is indicated at the top of FIG. 12A. In all cases, the identical amount of template DNAs was used for each transcription reactions. Therefore, the amount of 5' CAR (5' Cis-Acting Ribozyme; the transcribed fragment, initiated at the promoter and terminated by the cleavage action of the first 5' processing ribozyme, that is produced only once per each transcription cycle) (band 5) is identical in each cases, confirming the uniformed amount and purity of each templates. Similarly, the intensities of band 2, consisting of 5' CAR and trans-acting ribozyme for tat-1, are equal in all cases and independent of the unit numbers (n) because this segment is also transcribed into only one molecule per each template per one transcription reaction. This fragment is discernible since in our construct 5' CAR is less reactive than 3' CAR due to the presence of 2nd binding site for 5' CAR.

Figure 12B:
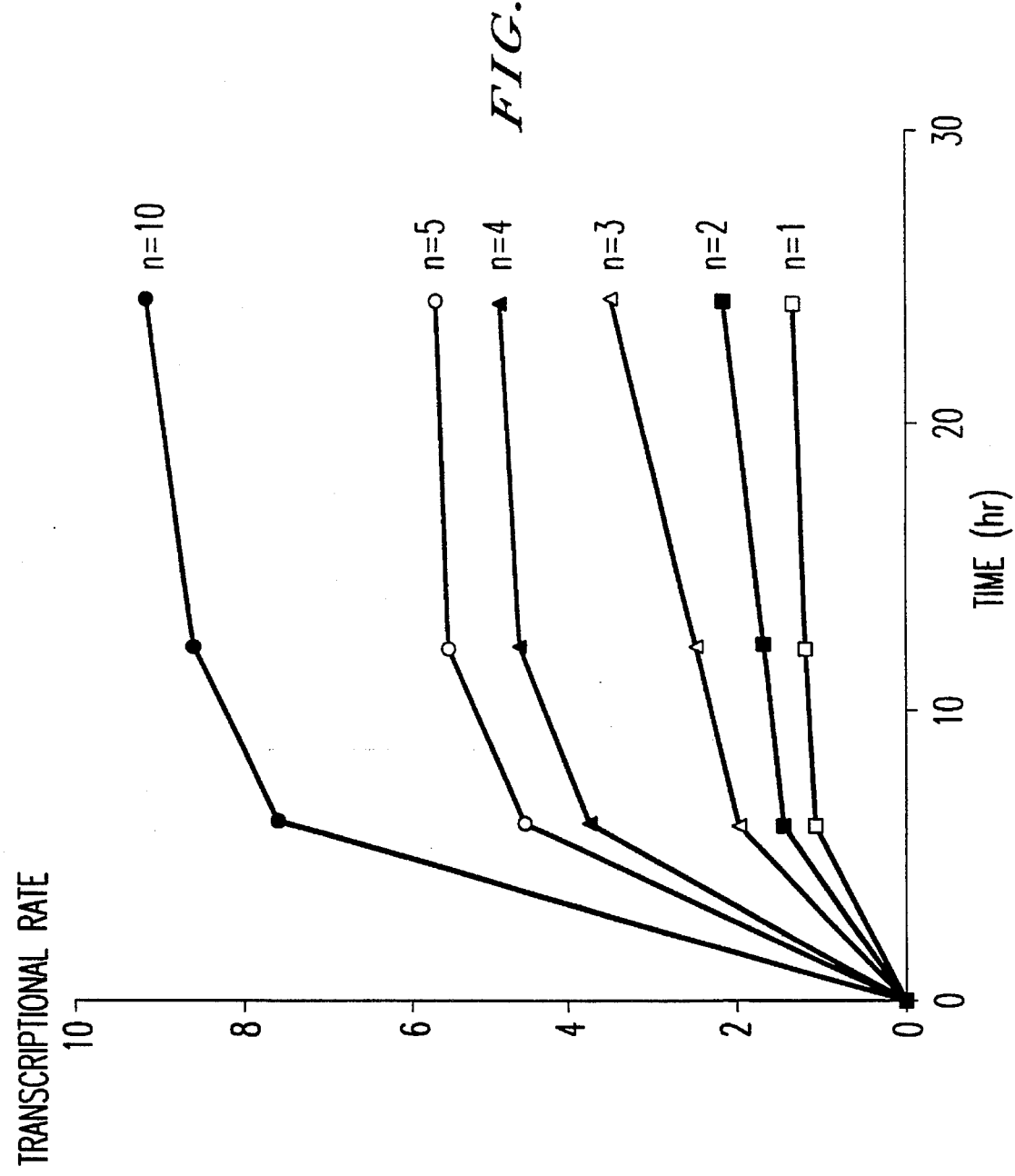

In contrast to the above mentioned bands 2 and 5, the amount of trans-acting ribozymes targeted to tat-1 (band 3) linearly increases in proportion to the connected units (n). Similarly, band 4, consisting of 5' CAR and 3' CAR, and band 1 of partially processed (3' processed) fragment increase with n. Therefore, by keeping the amount of template DNAs constant, it is still possible to increase the amount of transcripts merely by repeating the same units in the form of FIG. 11B. The proportionality is independent of the time at which samplings were made (FIG. 12B). Namely, the shotgun-type plasmid of n=10 always produces roughly 10-times higher quantities of trans-acting ribozymes than the plasmid of n=1. Since all these plasmids can stably be produced in E. coli cells, n can be increased further.

Figures 10A, 10B:
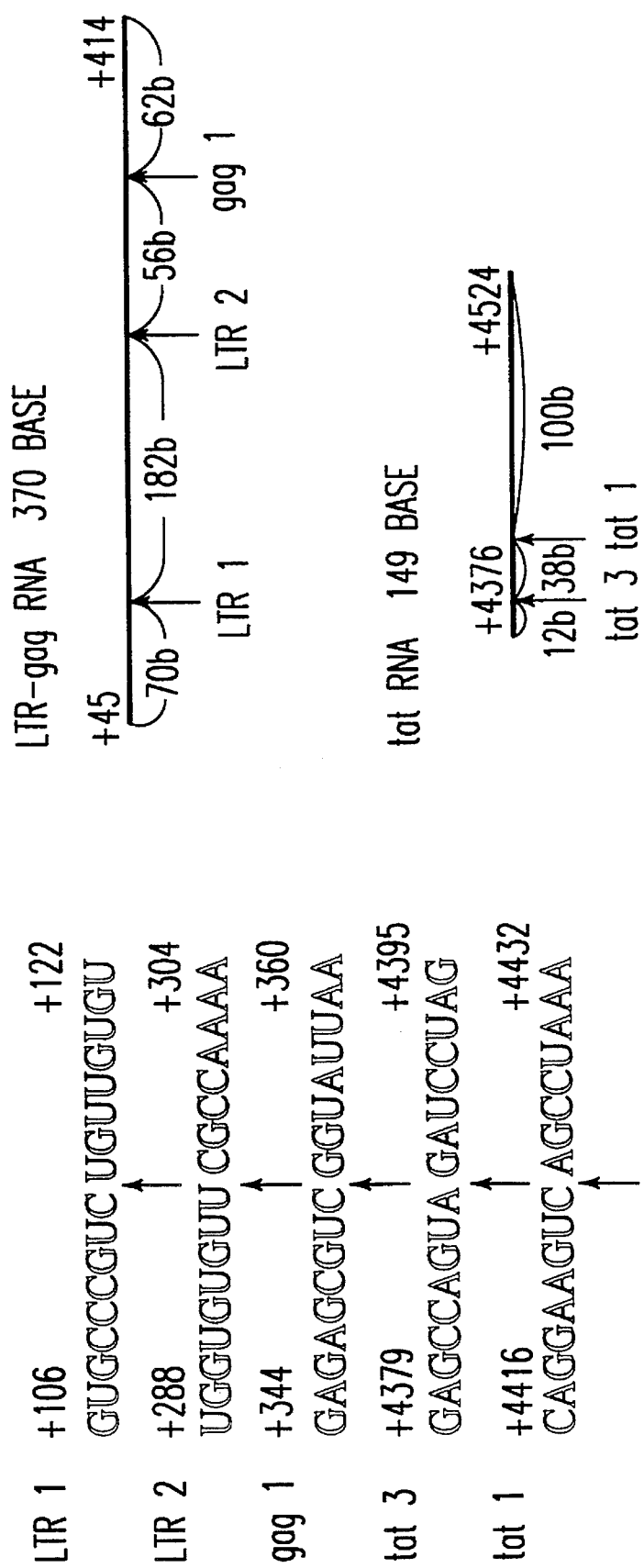
FIG. 10A shows five relatively conserved sites of HIV RNA (SEQ ID NOS:12–16), that are targeted by shotgun-type ribozymes. (B):HIV-1 RNA substrates used for co-transcriptional cleavage reactions. Target sites are indicated by arrows.

F. Comparison of Cleavage Activities between the Connected-Type and Shotgun-Type Ribozymes There are at least two ways to express multitargeted-ribozymes: the simpler way is just to join several sequences of multitargeted-ribozymes in tandem, so that all the transcribed multitargeted-ribozymes would be connected in tandem into a single RNA (connected-type, FIG. 11A); the other strategy is to combine cis-acting ribozymes with trans-acting ribozymes so that the several trans-acting ribozymes targeted to HIV would be trimmed at both 5' and 3'-ends by the actions of cis-acting ribozymes, liberating several trans-acting ribozymes which would work independently of others (shotgun-type, FIG. 11B). We keep two kinds of cis-acting ribozymes per a unit because their stem II and its loop region can be used to insert two kinds of activator trapping sequences such as tat and rev. Since the level of transcription for the shotgun-type plasmids was proportional to n (FIG. 12), the cleavage activity was also expected to be proportional to n. In order to (i) verify this expectation, and also to (ii) compare the activities with the connected-type transcripts, cleavage reactions were carried out in vitro (FIG. 13). In these experiments, transcription reactions were carried out under the identical conditions, as discussed in the previous section, except for the presence of gel-purified HIV-1 tat RNA fragment (FIG. 10B).

Figure 13A:
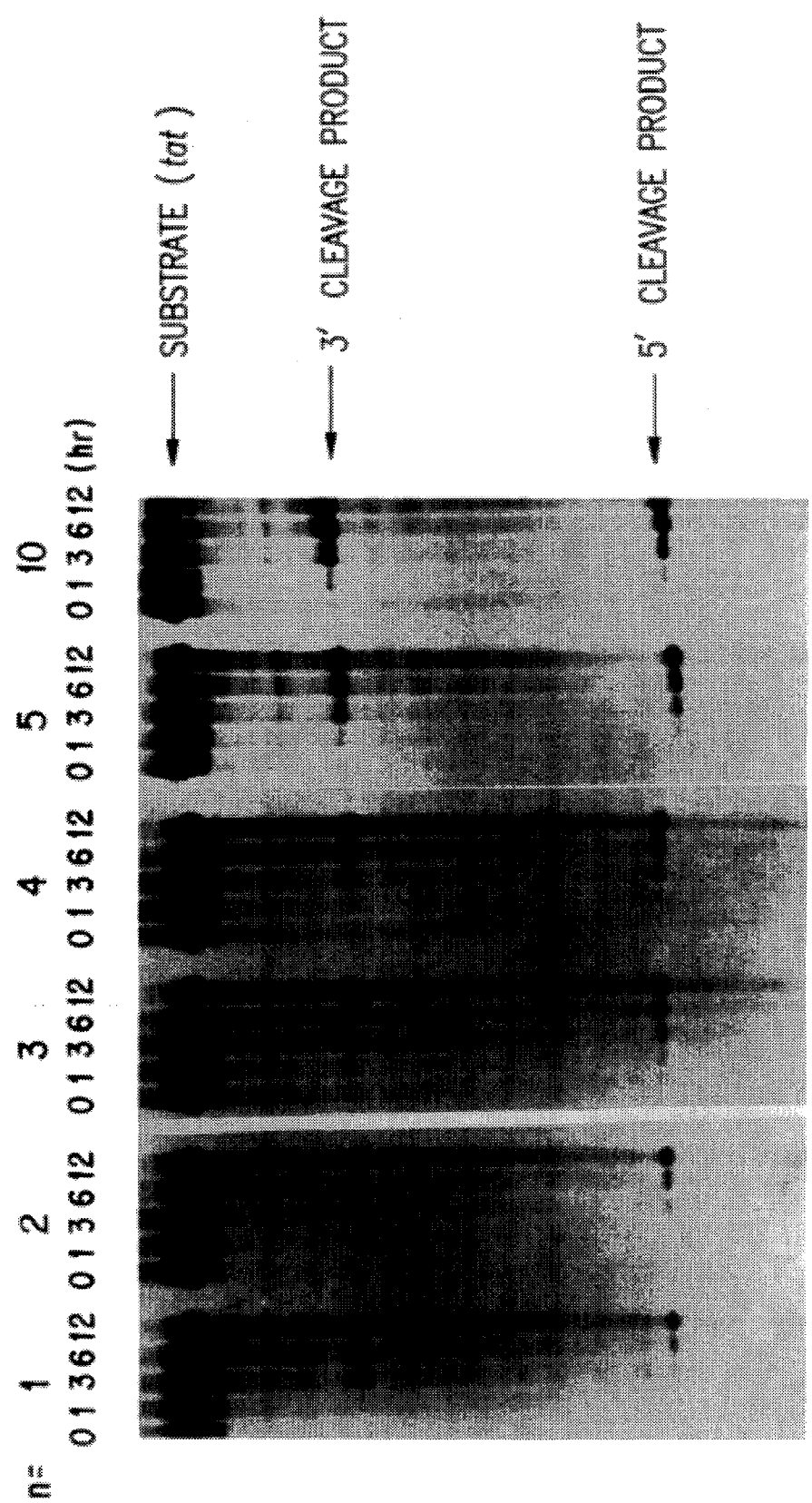
FIG. 13 shows co-transcriptional cleavage of HIV-1RNA possessing tat sequence (shown as tat RNA in FIG. 10B) by shotgun-type ribozymes. The cleavage activity is proportional to the number of units (n) connected in tandem. (A): Gel eleotrophoresis analysis of the co-transcriptional cleavages. (B): Relative rates of cleavage of tat RNA by ribozymes transcribed from the templates with n=1-10, measured at 6 h after the initiation of transcription. (C): Comparison of the cleavage activities between the connected-type ribozyme expression system (●and the shotgun-type ribozyme expression system (0), measured at 6 h after the initiation of transcription. The percentage of the cleaved products linearly increases with n in the case of shotgun-type ribozyme expression system (0), whereas the cleavage activity reaches plateau at around n=3 in the case of connected-type ribozyme expression system (● and thus templates with higher n do not contribute to a higher activity.
Figure 13B:
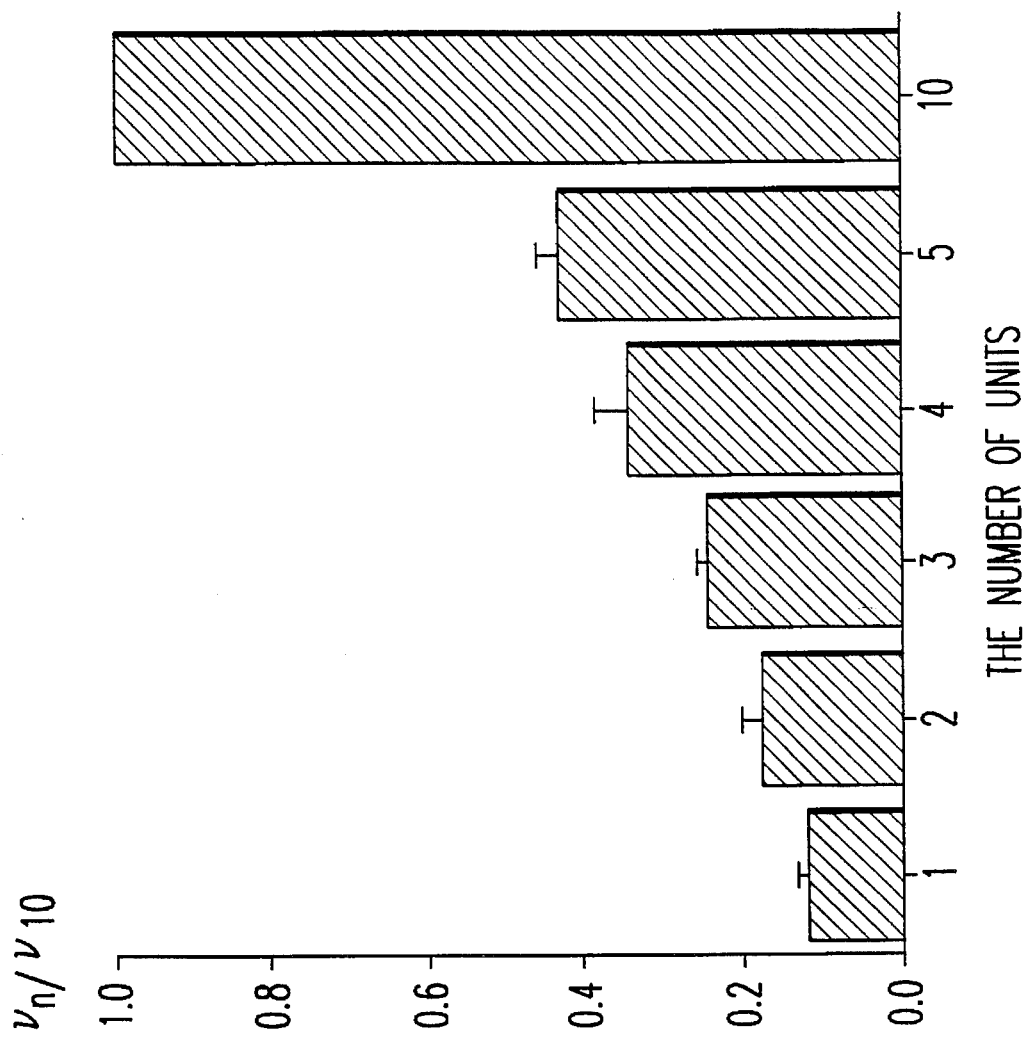
Figure 13C:
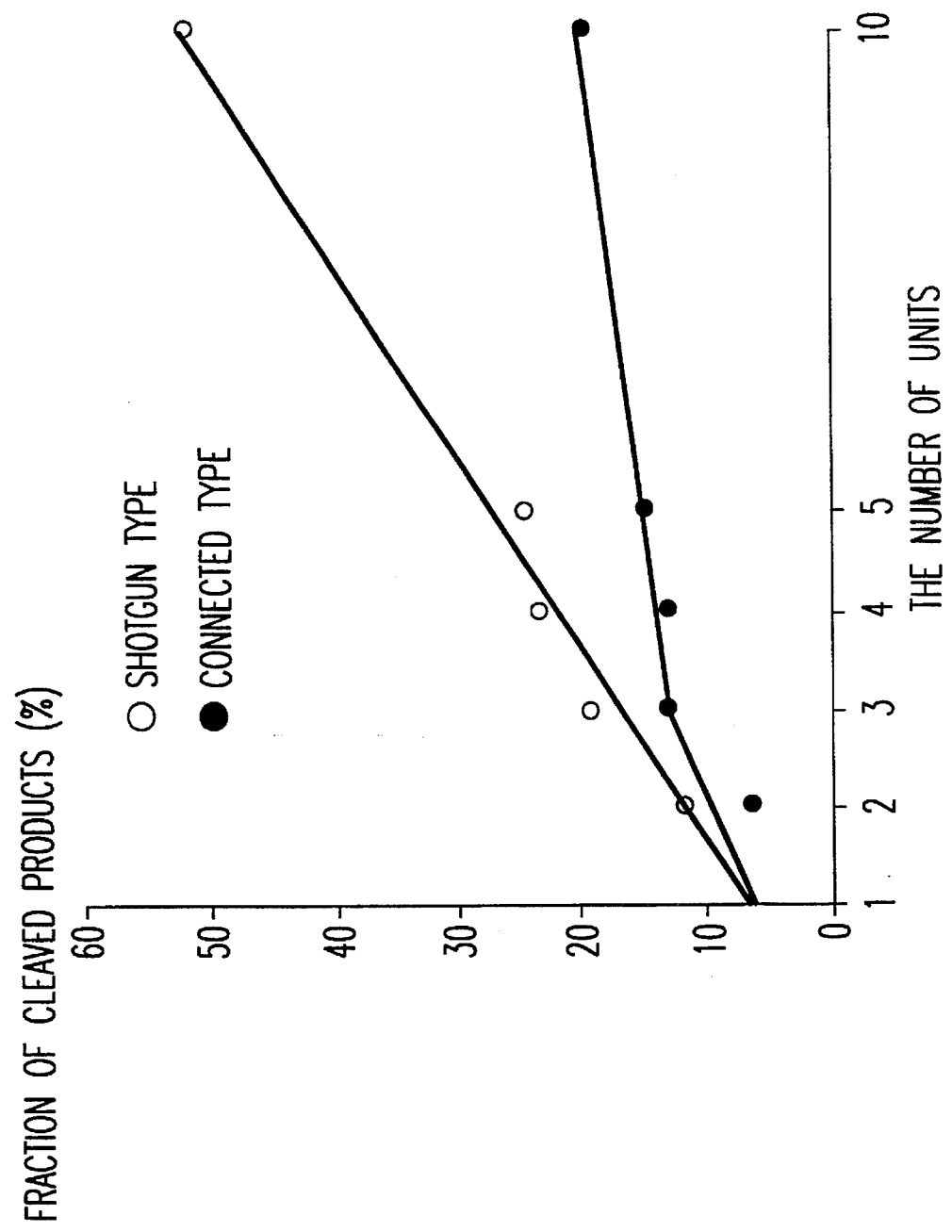

Decay of the HIV-1 tat RNA fragment was followed (FIG. 13A). Results revealed that, as we expected, the cleavage activities of the shotgun-type plasmids varying n=1–10), measured at 6 h incubation time, were proportional to n (FIG. 13B). On the other hand, the activity of the connected-type ribozyme (FIG. 11A) linearly increased up to n=3, thereafter, the activity no longer increased even at a larger n (see the saturation behavior in FIG. 13C). In order to facilitate the analysis of the transcription products, even for the connected-type construct, one 3' processing ribozyme was inserted at the extreme 3' terminus region as shown in FIG. 11A. Since the binding site sequence of the 3' processing ribozyme also existed at each internal regions, between the tRNA-embedded ribozymes, our connected-type plasmid (e.g., n=10) also produced some ribozymes smaller than the expected sizes (n=1–9). Since the activities of the connected-type ribozymes shown in FIG. 13C represent the overall activities (including the activities of those smaller independent ribozymes of n=1, 2, - - - ), the actual activities of the full-length connected type ribozymes are lower than that expected from the saturation curve of FIG. 13C.

These results clearly indicate that, in order to maintain the activity of ribozymes in proportion to the connected units (n), it is necessary to produce independent ribozymes. This conclusion should also be applicable to multitargeted-ribozymes in which 4 or more ribozymes, each possessing different target site, are to be used in vivo in order to overcome the mutability of HIV.

G. Expression Plasmids for Multitargeted-Ribozymes

Figure 14:
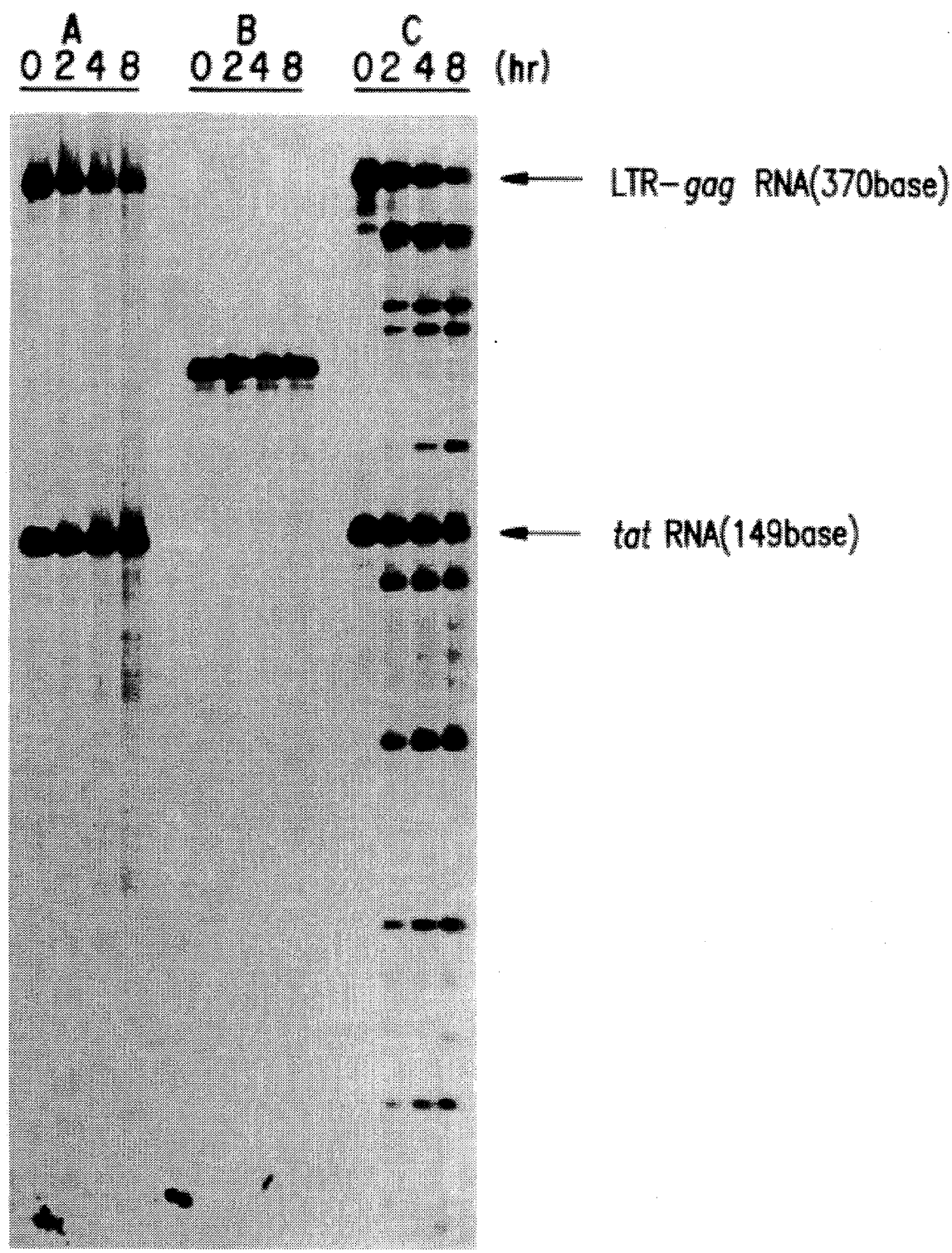
FIG. 14 shows co-transcriptional cleavage of two types of HIV-1 RNA (tat RNA and LTR-gag RNA in FIG. 10B) by a shotgun-type ribozyme expression vector that codes for five different ribozymes targeted to five different sites as shown in FIG. 10. Control experiment is shown in A in which two types of $^{32}$P-labeled HIV-1 RNA (tat RNA and LTR-gag RNA) alone were incubated in the absence of shotgun-type ribozyme expression vector. Another control reaction is shown in B in which $^{32}$P-labeled RNA substrate lacking the target sites was incubated with the shotgun-type ribozyme expression vector under transcriptional conditions. (C): Two types of $^{32}$P-labeled HIV-1 RNA (tat RNA and LTR-gag RNA) were incubated with the shotgun-type ribozyme expression vector, and the formation of the cleavage products of defined sizes were confirmed.

Considering the usage of shotgun-type ribozymes in vivo, several multitargeted-ribozymes expression vectors were constructed. Such plasmids contain 1–5 different binding sites (shown in FIG. 10A) (SEQ ID NOS:12–16). Transcription and cleavage assay were carried out nearly the same conditions as described in the previous section. Three sets of experiments using a multitargeted-ribozymes expression vector possessing 5 different target sites were shown in FIG. 14: Set A contains all the reagents including the two kinds of substrate RNAs necessary to examine the cleavage reactions except for the ribozyme plasmid (control A); In set B, the two substrate RNAs were replaced by a wrong substrate lacking the cleavage site, however, ribozyme plasmid was added (control B); Set C contains correct substrates and the ribozyme plasmid. Reactions were followed at 0, 2, 4, 8 h incubations. Since only the set C produced the expected cleavage products, the high substrate-specificity has been confirmed. Since each ribozymes possessing different target sites work independently of others, this kind of multitargeted-ribozymes must have high potential in the treatment of HIV.

E. coli strain JM109 carrying plasmid pGENE8459v3 was deposited with Fermentation Research Institute, Agency of Industrial Science and Technology and was assigned the accession number FERM BP-3331.

What is claimed is:

1. A recombinant plasmid containing a sequence encoding a trans-acting hammerhead-type ribozyme flanked by 5' and 3' self-cleaving cis-acting hammerhead ribozymes, which produces an RNA transcript that undergoes self-catalyzed cleavage at the 5' and 3' sides of said trans-acting ribozyme.

2. A recombinant plasmid containing 2–100 units of a sequence encoding a trans-acting hammerhead ribozyme flanked by 5' and 3' self-cleaving hammerhead ribozymes, which produces an equivalent number of units of RNA transcripts connected in tandem which subsequently undergo self-catalyzed cleavage at the 5' and 3' sides of each trans-acting ribozyme.

3. A method of producing RNA transcripts self-cleaved at 5' and 3' sides comprising: subjecting the recombinant plasmid of claim 1 to transcription conditions and collecting self-cleaved RNA transcripts.

4. A method of producing RNA transcripts self-cleaved at 5' and 3' sides comprising: subjecting the recombinant plasmid of claim 2 to transcription conditions and collecting self-cleaved RNA transcripts.

5. A transformant comprising a cultural bacteria cell, animal cell or plant cell which has been transformed with the recombinant plasmid of claim 1.

6. A transformant comprising a cultural bacteria cell, animal cell or plant cell which has been transformed with the recombinant plasmid of claim 2.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: unknown ( i i ) MOLECULE TYPE: mRNA ( x i ) SEQUENCE DESCRIPTION: SEQ ID NO:1:

CUGAUGAGUC CGUGAGGACG AAAC 24

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: unknown
        ( D ) TOPOLOGY: unknown ( i i ) MOLECULE TYPE: mRNA ( x i ) SEQUENCE DESCRIPTION: SEQ ID NO:2:

GAACAAACGA CCACAACCCG GG 22

( 2 ) INFORMATION FOR SEQ ID NO:3:

( i ) SEQUENCE CHARACTERISTICS:
        ( A ) LENGTH: 159 base pairs
        ( B ) TYPE: nucleic acid
        ( C ) STRANDEDNESS: unknown
        ( D ) TOPOLOGY: unknown ( i i ) MOLECULE TYPE: mRNA ( v i ) ORIGINAL SOURCE:
        ( A ) ORGANISM: yeast ( i x ) FEATURE:
        ( A ) NAME/KEY: misc_structure
        ( B ) LOCATION: 8..29

( i x ) FEATURE:
        ( A ) NAME/KEY: misc_binding
        ( B ) LOCATION: 34..54

( i x ) FEATURE:
        ( A ) NAME/KEY: misc_binding
        ( B ) LOCATION: 59..96

( i x ) FEATURE:
        ( A ) NAME/KEY: misc_structure
        ( B ) LOCATION: 67..88

( i x ) FEATURE:
                ( A ) NAME/KEY: misc_binding
                ( B ) LOCATION: 99..114

( i x ) FEATURE:
                ( A ) NAME/KEY: misc_structure
                ( B ) LOCATION: 127..148

( x i ) SEQUENCE DESCRIPTION: SEQ ID NO:3:

TCGAGCTCTG ATGAGTCCGT GAGGACGAAA CGGTACCCGG TACCGTCAGC TCGAGCTCAA    60

CTGGTGCTGA TGAGTCCGTG AGGACGAAAC GGGTCTGACG GATCCGTCGA CGGATCTAGA    120

TCCGTCCTGA TGAGTCCGTG AGGACGAAAC GGATCTGCA                           159

( 2 ) INFORMATION FOR SEQ ID NO:4:

( i ) SEQUENCE CHARACTERISTICS:
                ( A ) LENGTH: 61 base pairs
                ( B ) TYPE: nucleic acid
                ( C ) STRANDEDNESS: unknown
                ( D ) TOPOLOGY: unknown ( i i ) MOLECULE TYPE: mRNA ( x i ) SEQUENCE DESCRIPTION: SEQ ID NO:4:

AGCUCGAGCU CAACUGGUGC UGAUGAGUCC GUGAGGACGA AACGGGUCUG ACGGAUCCGU    60

C                                                                    61

( 2 ) INFORMATION FOR SEQ ID NO:5:

( i ) SEQUENCE CHARACTERISTICS:
                ( A ) LENGTH: 58 base pairs
                ( B ) TYPE: nucleic acid
                ( C ) STRANDEDNESS: unknown
                ( D ) TOPOLOGY: circular ( i i ) MOLECULE TYPE: mRNA ( i x ) FEATURE:
                ( A ) NAME/KEY: misc_structure
                ( B ) LOCATION: 8..29

( x i ) SEQUENCE DESCRIPTION: SEQ ID NO:5:

TCGAGCTCTG ATGAGTCCGT GAGGACGAAA CGGTACCCGG TACCGTCAGC TCGAGCTC     58

( 2 ) INFORMATION FOR SEQ ID NO:6:

( i ) SEQUENCE CHARACTERISTICS:
                ( A ) LENGTH: 60 base pairs
                ( B ) TYPE: nucleic acid
                ( C ) STRANDEDNESS: unknown
                ( D ) TOPOLOGY: circular ( i i ) MOLECULE TYPE: mRNA ( i x ) FEATURE:
                ( A ) NAME/KEY: misc_structure
                ( B ) LOCATION: 28..49

( x i ) SEQUENCE DESCRIPTION: SEQ ID NO:6:

GGATCCGTCG ACGGATCTAG ATCCGTCCTG ATGAGTCCGT GAGGACGAAA CGGATCTGCA    60

( 2 ) INFORMATION FOR SEQ ID NO:7:

( i ) SEQUENCE CHARACTERISTICS:
                ( A ) LENGTH: 58 base pairs
                ( B ) TYPE: nucleic acid
                ( C ) STRANDEDNESS: unknown
                ( D ) TOPOLOGY: unknown ( i i ) MOLECULE TYPE: cDNA to mRNA ( x i ) SEQUENCE DESCRIPTION: SEQ ID NO:7:

TCGAGCTCTG ATGAGTCCGT GAGGACGAAA CGGTAGCCGC TACCGTCAGC TCGAGCTC 58

( 2 ) INFORMATION FOR SEQ ID NO:8:

( i ) SEQUENCE CHARACTERISTICS:
        ( A ) LENGTH: 32 base pairs
        ( B ) TYPE: nucleic acid
        ( C ) STRANDEDNESS: unknown
        ( D ) TOPOLOGY: unknown ( i i ) MOLECULE TYPE: cDNA to mRNA ( x i ) SEQUENCE DESCRIPTION: SEQ ID NO:8:

ATCAGAGTGC GCAGCGGAAG CGTGGTGGGC CC 32

( 2 ) INFORMATION FOR SEQ ID NO:9:

( i ) SEQUENCE CHARACTERISTICS:
        ( A ) LENGTH: 49 base pairs
        ( B ) TYPE: nucleic acid
        ( C ) STRANDEDNESS: unknown
        ( D ) TOPOLOGY: unknown ( i i ) MOLECULE TYPE: cDNA to mRNA ( x i ) SEQUENCE DESCRIPTION: SEQ ID NO:9:

CCGAAGCGAA CTGATGAGTC GGTGACCGAC GAAACCTCTC GGAGATATC 49

( 2 ) INFORMATION FOR SEQ ID NO:10:

( i ) SEQUENCE CHARACTERISTICS:
        ( A ) LENGTH: 64 base pairs
        ( B ) TYPE: nucleic acid
        ( C ) STRANDEDNESS: unknown
        ( D ) TOPOLOGY: unknown ( i i ) MOLECULE TYPE: cDNA to mRNA ( x i ) SEQUENCE DESCRIPTION: SEQ ID NO:10:

CCATAACCCA CAGGTCCCAG GATCGAAACC TGGCTCTGAT AAAAAAAAAA AAAAAAAAAA 60

AAAA 64

( 2 ) INFORMATION FOR SEQ ID NO:11:

( i ) SEQUENCE CHARACTERISTICS:
        ( A ) LENGTH: 61 base pairs
        ( B ) TYPE: nucleic acid
        ( C ) STRANDEDNESS: unknown
        ( D ) TOPOLOGY: unknown ( i i ) MOLECULE TYPE: cDNA to mRNA ( x i ) SEQUENCE DESCRIPTION: SEQ ID NO:11:

AAAAAAGTCG AGGGCTCTAG AGCCCTCCTG ATGAGTCCGT GAGGACGAAA CTTTTTTTGC 60

A 61

( 2 ) INFORMATION FOR SEQ ID NO:12:

( i ) SEQUENCE CHARACTERISTICS:
        ( A ) LENGTH: 17 base pairs
        ( B ) TYPE: nucleic acid
        ( C ) STRANDEDNESS: unknown
        ( D ) TOPOLOGY: unknown ( i i ) MOLECULE TYPE: RNA (genomic)

( x i ) SEQUENCE DESCRIPTION: SEQ ID NO:12:

GUGCCCGUCU GUUGUGU 17

( 2 ) INFORMATION FOR SEQ ID NO:13:

( i ) SEQUENCE CHARACTERISTICS:
( A ) LENGTH: 17 base pairs
( B ) TYPE: nucleic acid
( C ) STRANDEDNESS: unknown
( D ) TOPOLOGY: unknown ( i i ) MOLECULE TYPE: RNA (genomic)

( x i ) SEQUENCE DESCRIPTION: SEQ ID NO:13:

UGGUGUGUUC GCCAAAA 17

( 2 ) INFORMATION FOR SEQ ID NO:14:

( i ) SEQUENCE CHARACTERISTICS:
( A ) LENGTH: 17 base pairs
( B ) TYPE: nucleic acid
( C ) STRANDEDNESS: unknown
( D ) TOPOLOGY: unknown ( i i ) MOLECULE TYPE: RNA (genomic)

( x i ) SEQUENCE DESCRIPTION: SEQ ID NO:14:

GAGAGCGUCG GUAUUAA 17

( 2 ) INFORMATION FOR SEQ ID NO:15:

( i ) SEQUENCE CHARACTERISTICS:
( A ) LENGTH: 17 base pairs
( B ) TYPE: nucleic acid
( C ) STRANDEDNESS: unknown
( D ) TOPOLOGY: unknown ( i i ) MOLECULE TYPE: RNA (genomic)

( x i ) SEQUENCE DESCRIPTION: SEQ ID NO:15:

GAGCCAGUAG AUCCUAG 17

( 2 ) INFORMATION FOR SEQ ID NO:16:

( i ) SEQUENCE CHARACTERISTICS:
( A ) LENGTH: 17 base pairs
( B ) TYPE: nucleic acid
( C ) STRANDEDNESS: unknown
( D ) TOPOLOGY: unknown ( i i ) MOLECULE TYPE: RNA (genomic)

( x i ) SEQUENCE DESCRIPTION: SEQ ID NO:16:

CAGGAAGUCA GCCUAAA 17